US009315549B2

(12) United States Patent
Vazquez-Cintron et al.

(10) Patent No.: US 9,315,549 B2
(45) Date of Patent: Apr. 19, 2016

(54) TREATMENT METHODS USING ATOXIC NEUROTOXIN DERIVATIVES

(71) Applicants: Edwin J. Vazquez-Cintron, New York, NY (US); Konstantin Ichtchenko, Brooklyn, NY (US); Philip A. Band, West Orange, NJ (US)

(72) Inventors: Edwin J. Vazquez-Cintron, New York, NY (US); Konstantin Ichtchenko, Brooklyn, NY (US); Philip A. Band, West Orange, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 14/166,434

(22) Filed: Jan. 28, 2014

(65) Prior Publication Data

US 2014/0212456 A1 Jul. 31, 2014

Related U.S. Application Data

(60) Provisional application No. 61/757,478, filed on Jan. 28, 2013.

(51) Int. Cl.
*A61K 38/48* (2006.01)
*C07K 14/00* (2006.01)
*C07K 14/33* (2006.01)
*C12N 9/52* (2006.01)

(52) U.S. Cl.
CPC ........... *C07K 14/001* (2013.01); *A61K 38/4893* (2013.01); *C07K 14/33* (2013.01); *C12N 9/52* (2013.01); *C12Y 304/24069* (2013.01); *C07K 2319/50* (2013.01)

(58) Field of Classification Search
None
See application file for complete search history.

(56) References Cited

U.S. PATENT DOCUMENTS

| | | | |
|---|---|---|---|
| 5,750,383 A | 5/1998 | Blissard et al. | |
| 5,846,929 A | 12/1998 | Johnson et al. | |
| 5,919,665 A | 7/1999 | Williams | |
| 5,939,070 A | 8/1999 | Johnson et al. | |
| 6,001,806 A | 12/1999 | Hilbert et al. | |
| 6,022,950 A | 2/2000 | Murphy | |
| 6,037,150 A | 3/2000 | Latrou et al. | |
| 6,051,239 A | 4/2000 | Simpson et al. | |
| 6,203,794 B1 | 3/2001 | Dolly et al. | |
| 6,261,561 B1 | 7/2001 | Stewart, Jr. et al. | |
| 6,323,023 B1 | 11/2001 | Shoseyov et al. | |
| 6,461,617 B1 | 10/2002 | Shone et al. | |
| 6,787,517 B1 | 9/2004 | Gil et al. | |
| 6,831,059 B2 | 12/2004 | Donovan | |
| 6,852,510 B2 | 2/2005 | Bremel et al. | |
| 6,881,411 B2 | 4/2005 | Stewart, Jr. et al. | |
| 6,967,088 B1 | 11/2005 | Williams et al. | |
| 7,132,259 B1 | 11/2006 | Dolly et al. | |
| 7,172,764 B2 | 2/2007 | Li et al. | |
| 7,223,577 B2 | 5/2007 | Steward et al. | |
| 7,227,010 B2 | 6/2007 | Smith | |
| 7,273,722 B2 | 9/2007 | Lin et al. | |
| 7,419,676 B2 | 9/2008 | Dolly et al. | |
| 7,422,877 B2 | 9/2008 | Dolly et al. | |
| 7,456,272 B2 | 11/2008 | Lin et al. | |
| 7,632,251 B2 | 12/2009 | Lin et al. | |
| 7,658,933 B2 | 2/2010 | Foster et al. | |
| 7,785,606 B2 | 8/2010 | Ichtchenko et al. | |
| 7,888,469 B2 | 2/2011 | Steward et al. | |
| 7,893,202 B1 | 2/2011 | Steward et al. | |
| 8,044,188 B2 | 10/2011 | Ichtchenko et al. | |
| 8,119,767 B2 | 2/2012 | Steward et al. | |
| 2001/0016199 A1 | 8/2001 | Johnston et al. | |
| 2002/0107199 A1 | 8/2002 | Walker | |
| 2002/0137886 A1 | 9/2002 | Lin et al. | |
| 2002/0168727 A1 | 11/2002 | Smith et al. | |
| 2002/0177545 A1 | 11/2002 | Donovan | |
| 2003/0027752 A1 | 2/2003 | Steward et al. | |
| 2003/0049264 A1 | 3/2003 | Foster et al. | |
| 2003/0100071 A1 | 5/2003 | Apicella et al. | |
| 2003/0143651 A1 | 7/2003 | Steward et al. | |
| 2003/0166238 A1 | 9/2003 | Shone et al. | |
| 2003/0215468 A1 | 11/2003 | Williams et al. | |
| 2003/0219402 A1 | 11/2003 | Rutter | |
| 2003/0229454 A1 | 12/2003 | Reinherz et al. | |
| 2004/0013687 A1 | 1/2004 | Simpson et al. | |
| 2004/0018589 A1 | 1/2004 | Zhong | |
| 2004/0052819 A1 | 3/2004 | Kingsley et al. | |
| 2004/0071736 A1 | 4/2004 | Quinn et al. | |
| 2004/0101531 A1 | 5/2004 | Curtiss, III et al. | |
| 2004/0115215 A1 | 6/2004 | Williams | |
| 2004/0115727 A1 | 6/2004 | Steward et al. | |
| 2004/0220386 A1 | 11/2004 | Steward et al. | |
| 2004/0235118 A1 | 11/2004 | Williams | |
| 2005/0060762 A1 | 3/2005 | Bleck | |
| 2005/0106182 A1 | 5/2005 | Li et al. | |

(Continued)

FOREIGN PATENT DOCUMENTS

| | | |
|---|---|---|
| EP | 0209281 | 1/1987 |
| WO | WO 98/07864 | 2/1998 |
| WO | WO 01/18038 A2 | 3/2001 |
| WO | WO 0114570 | 3/2001 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
National Institute of Allergy and Infectious Diseases, "NIAID Biodefense Research Agenda for CDC Category A Agents. Progress Report," NIH Publication # 03-5432, pp. 1-37 (2003).

(Continued)

*Primary Examiner* — Brian J Gangle
(74) *Attorney, Agent, or Firm* — LeClairRyan, a Professional Corporation

(57) ABSTRACT

The present invention relates to a treatment method. This method involves contacting a subject with an isolated, physiologically active, atoxic derivative of a Clostridial neurotoxin. Contacting is carried out to treat the subject. The derivative of a Clostridial neurotoxin does not possess a cargo attachment peptide sequence at its N-terminus.

21 Claims, 4 Drawing Sheets

(56) References Cited

U.S. PATENT DOCUMENTS

| | | |
|---|---|---|
| 2005/0260230 A1 | 11/2005 | Steward et al. |
| 2006/0024794 A1 | 2/2006 | Li et al. |
| 2006/0039929 A1 | 2/2006 | Fernandez-Salas et al. |
| 2006/0204524 A1 | 9/2006 | Ichtchenko et al. |
| 2007/0104737 A1 | 5/2007 | Smith |
| 2008/0057575 A1 | 3/2008 | Fernandez-Salas et al. |
| 2011/0206616 A1 | 8/2011 | Ichtchenko et al. |

OTHER PUBLICATIONS

Abrams, P., "The Role of Neuromodulation in the Management of Urinary Urge Incontinence," *BJU Int.* 93(7):1116 (2004).
Achem, S.R., "Treatment of Spastic Esophageal Motility Disorders," *Gastroenterol Clin. North Am.* 33(1):107-124 (2004).
Adler et al., "Botulinum Toxin Type A for Treating Voice Tremor," *Arch. Neurol.* 61(9):1416-1420 (2004).
Agarwal et al., "Structural Analysis of Botulinum Neurotoxin Type E Catalytic Domain and Its Mutant Glu212→Gln Reveals the Pivotal Role of the Glu212 Carboxylate in the Catalytic Pathway," *Biochemistry* 43(21):6637-6644 (2004).
Ahn et al., "Botulinum Toxin for Masseter Reduction in Asian Patients," *Arch. Facial Plast. Surg.* 6(3):188-191 (2004).
Aoki, K.R., "Evidence for Antinociceptive Activity of Botulinum Toxin Type A in Pain Management," *Headache* 43(Suppl 1):S9-S15 (2003).
Aquilina et al., "Reduction of a Chronic Bilateral Temporomandibular Joint Dislocation with Intel-maxillary Fixation and Botulinum Toxin A," *Br J. Oral Maxillolac. Surg.* 42(3):272-273 (2004).
Bach-Rojecky & Lacković, "Antinociceptive Effect of Botulinum Toxin Type A in Rat Model of Carrageenan and Capsaicin Induced Pain," *Croat. Med. J.* 46(2):201-208 (2005).
Bade et al., "Botulinum Neurotoxin Type D Enables Cytosolic Delivery of Enzymatically Active Cargo Proteins to Neurons via Unfolded Translocation Intermediates," *J. Neurochem.* 91(6):1461-1472 (2004).
Bakheit, A.M., "Optimizing the Methods of Evaluation of the Effectiveness of Botulinum Toxin Treatment of Post-Stroke Muscle Spasticity," *J. Neurol. Neurosurg. Psychiatry* 75:665-666 (2004).
Balkrishnan et al., "Longitudinal Examination of Health Outcomes Associated with Botulinum Toxin Use in Children with Cerebral Palsy," *J. Surg. Orthop. Adv.* 13:76-80 (2004).
Bayles & Deschler, "Operative Prevention and Management of Voice-Limiting Pharyngoesophageal Spasm," *Otolaryngol Clin. North Am.* 37(3):547-558 (2004).
Bender et al., "Speech Intelligibility in Severe Adductor Spasmodic Dysphonia," *J. Speech Lang. Hear. Res.* 47(1):21-32 (2004).
Bentsianov et al., "Noncosmetic Uses of Botulinum Toxin," *Clin. Dermatol.* 22(1):82-88 (2004).
Berweck & Heinen, "Use of Botulinum Toxin in Pediatric Spasticity (Cerebral Palsy)," *Mov. Disord.* 19(Suppl 8)S162-S167 (2004).
Blersch et al., "Botulinum Toxin A and the Cutaneous Nociception in Humans: A Prospective, Double-Blind, Placebo-Controlled, Randomized Study," *J. Neurol. Sci.* 205(1):59-63 (2002).
Blumenfeld et al., "Botulinum Neurotoxin for the Treatment of Migraine and Other Primary Headache Disorders," *Dermatol. Clin.* 22(2):167-175 (2004).
Brandt & Boker, "Botulinum Toxin for the Treatment of Neck Lines and Neck Bands," *Dermatol. Clin.* 22(2):159-166 (2004).
Brisinda et al., "Botulinum Neurotoxin to Treat Chronic Anal Fissure: Results of a Randomized 'Botox vs. Dysport' Controlled Trial," *Aliment Pharmacol. Ther.*, 19(6):695-701 (2004).
Byrne et al., "Purification, Potency, and Efficacy of the Botulinum Neurotoxin Type A Binding Domain from *Pichia pastoris* as a Recombinant Vaccine Candidate," *Infect. Immun*. 66(10):4817-4822 (1998).
Caccin et al., "VAMP/Synaptobrevin Cleavage by Tetanus and Botulinum Neurotoxins is Strongly Enhanced by Acidic Liposomes," *FEBS Lett*. 542(1-3):132-136 (2003).
Capaccio et al., "Diagnosis and Therapeutic Management of Iatrogenic Parotid Sialocele," *Ann. Otol. Rhinol. Laryngol*. 113(7):562-564 (2004).
Carruthers & Carrutiiers,"Botox: Beyond Wrinkles," *Clin. Dermatol*. 22(1):89-93 (2004).
Carruthers & Carruthers, "Botulinum Toxin A in the Mid and Lower Face and Neck," *Dermatol. Clin*. 22(2):151-158 (2004).
Carruthers & Carruthers, "Botulinum Toxin Type A for the Treatment of Glabellar Rhytides," *Dermatol. Clin*. 22(2):137-144 (2004).
Chaddock et al., "Expression and Purification of Catalytically Active, Non-Toxic Endopeptidase Derivatives of *Clostridium botulinum* Toxin Type A," *Protein Expr. Purif*. 25(2):219-228 (2002).
Chaddock ct al., "Retargeted Clostridial Endopeptidases. Inhibition of Nociceptive Neurotransmitter Release In Vitro, and Antinociceptive Activity in In Vivo Models of Pain," Mov. Disord. 19(Suppl 8):S42-S47 (2004).
Chao et al., "Management of Pharyngoesophageal Spasm with Botox," *Otolaryngol Clin. North Am*. 37(3):559-566 (2004).
Chen et al., "Altering Brow Contour with Botulinum Toxin," *Facial Plast. Surg. Clin. N. Am*. 11:457-464 (2003).
Cruz, F., "Mechanisms Involved in New Therapies for Overactive Bladder," *Urology* 63(Suppl 3A):65-73 (2004).
Cui et al., "Subcutaneous Administration of Botulinum Toxin A Reduces Formalin-Induced Pain," *Pain* 107:(1-2):125-133 (2004).
Defazio & Livrea, "Primary Blepharospasm: Diagnosis and Management," *Drugs* 64(3):237-244 (2004).
Dekleva & DasGupta, "Nicking of Single Chain Clostridium Botulinum Type A Neurotoxin by an Endogenous Protease," *Biochem. Biophys. Res*. Commun. 162(2):767-772 (1989).
Derman et al., "Mutations That Allow Disulfide Bond Formation in the Cytoplasm of *Escherichia coli*," *Science* 262(5140):1744-1747 (1993).
Dolly et al., "Acceptors for Botulinum Neurotoxin Reside on Motor Nerve Terminals and Mediate Its Internalization," *Nature* 307(5950):457-460 (1984).
Dong et al., "Synaptotagmins I and II Mediate Entry of Botulinum Neurotoxin B Into Cells," *J. Cell. Biol*. 162(7):1293-1303 (2003).
Eleopra et al., "Different Types of Botulinum Toxin in Humans," *Mov. Disord*. 19(Suppl 8)S53-S59 (2004).
Emonard et al., "Regulation of Matrix Metalloproteinase (MMP) Activity by the Low-Density Lipoprotein Receptor-Related Protein (LRP). A New Function for an 'Old Friend'," *Biochimie* 87(3-4):369-376 (2005).
Finn, J.C., "Botulinum Toxin Type A: Fine-Tuning Treatment of Facial Nerve Injury," *J. Drugs Dermatol*. 3(2):133-137 (2004).
Flynn, T.C., "Myobloc," *Dermatol. Clin*. 22(2):207-211 (2004).
Giannantoni et al., "Intravesical Resiniferatoxin Versus Botulinum-A Toxin Injections for Neurogenic Detrusor Overactivity: A Prospective Randomized Study," *J. Urol*. 172(1):240-243 (2004).
Glogau, R.G., "Treatment of Hyperhidrosis with Botulinum Toxin," *Dermatol. Clin*. 22(2):177-185 (2004).
Goodnough et al., "Development of a Delivery Vehicle for Intracellular Transport of Botulinum Neurotoxin Antagonists," *FEBS Lett*. 513(2-3):163-168 (2002).
Haussermann et al., "Long-Term Follow-Up of Cervical Dystonia Patients Treated with Botulinum Toxin A," *Mov. Disord*. 19(3):303-308 (2004).
Hayden et al., "Discovery and Design of Novel Inhibitors of Botulinus Neurotoxin A: Targeted 'Hinge' Peptide Libraries," *J. Appl. Toxicol*. 23(1):1-7 (2003).
Hoch et al., "Channels Formed by Botulinum, Tetanus, and Diphtheria Toxins in Planar Lipid Bilayers: Relevance to Translocation of Proteins Across Membranes," *Proc. Natl. Acad. Sci. USA* 82(6). 1692-1696 (1985).
Hojilla et al., "Matrix Metalloproteinases and Their Tissue Inhibitors Direct Cell Fate During Cancer Development," *Br. J. Cancer* 89(10):1817-1821 (2003).
Hyman et al., "Botulinum Toxin (*Dysport*®) Treatment of Hip Adductor Spasticity in Multiple Sclerosis: A Prospective, Randomised, Double Blind, Placebo Controlled, Dose Ranging Study," *J Neurol. Neurosurg. Psychiatry* 68(6):707-712 (2000).
Jankovic, J., "Botulinum Toxin in Clinical Practice," *J Neurol. Neurosurg. Psychiatry* 75(7):951-957 (2004).

(56) References Cited

OTHER PUBLICATIONS

Johnson, E.A., "Clostridial Toxins as Therapeutic Agents: Benefits of Nature's Most Toxic Proteins," *Annu. Rev. Microbiol.* 53:551-575 (1999).
Jost & Aoki, "Botulinum Toxin A in Anal Fissure: Why Does It Work?" *Dis. Colon Rectum.* 47(2):257-258 (2004).
Kadkhodayan et al., "Cloning, Expression, and One-Step Purification of the Minimal Essential Domain of the Light Chain of Botulinum Neurotoxin Type A," *Protein Expr. Purif.* 19(1):125-130 (2000).
Kern et al., "Effects of Botulinum Toxin Type B on Stump Pain and Involuntary Movements of the Stump," *Am. J. Phys. Med. Rehabil.* 83(5):396-399 (2004).
Ktyatktn et al., "Induction of an Titiimitic Response by Oral Administration of Recombinant Botulinum Toxin," *Infect. Immun.* 65(11):4586-4591 (1997).
Klein, A.W., "The Therapeutic Potential of Botulinum Toxin," *Dermatol. Surg.* 30(3):452-455 (2004).
Koriazova & Montal., "Translocation of Botulinum Neurotoxin Light Chain Protease Through the Heavy Chain Channel," *Nat. Struct. Biol.* 10(1):13-18 (2003).
Krämer et al., "Botulinum Toxin A Reduces Neurogenic Flare But Has Almost No Effect on Pain and Ilyperalgesia in human Skin," *J. Neurol.* 250(2):188-193 (2003).
Kurazono et al., "Minimal Essential Domains Specifying Toxicity of the Light Chains of Tetanus Toxin and Botulinum Neurotoxin Type A," *J Biol. Chem.* 267(21):14721-14729 (1992).
Kyrmizakis et al., "The Use of Botulinum Toxin Type A in the Treatment of Frey and Crocodile Tears Syndromes," *J. Oral Maxillofac. Surg.* 62(7):840-844 (2004).
Lacy et al., "Crystal Structure of Botulinum Neurotoxin Type A and Implications for Toxicity," *Nat. Struct. Biol.* 5(10):898-902 (1998).
Lacy & Stevens, "Recombinant Expression and Purification of the Botulinum Ncurotoxin Type A Translocation Domain," *Protein Expr. Purif.* 11(2):195-200 (1997).
Lalli et al., "Functional Characterisation of Tetanus and Botulinum Neurotoxins Binding Domains," *J. Cell Sci.* 112(Pt 16):2715-2724 (1999).
Lang, A., "History and Uses of Botox (Botulinum Toxin Type A)," *Lippincott's Case Manag.* 9(2):109-112 (2004).
Layeeque et al., "Botulinum Toxin Infiltration for Pain Control After Mastectomy and Expander Reconstruction," *Ann. Surg.* 240(4):608-614 (2004).
Lee et al., "A Case of Foul Genital Odor Treated with Botulinum Toxin A," *Dermatol. Surg.* 30(9):1233-1235 (2004).
Leippold et al., "Botulinum Toxin as a New Therapy Option for Voiding Disorders: Current State of the Art," *Eur. Urol.* 44(2):165-174 (2003).
Levy et al., "Botulinum Toxin A: A 9-Month Clinical and 3D In Vivo Profilometric Crow's Feet Wrinkle Formation Study," *J Cosmet. Laser Ther.* 6(1):16-20 (2004).
Li et al., "Recombinant Forms of Tetanus Toxin Engineered for Examining and Exploiting Neuronal Trafficking Pathways," *J. Biol. Chem.* 276(33):31394-31401 (2001).
Lozsadi et al., "Botulinum Toxin A Improves Involuntary Limb Movements in Rasmussen Syndrome," *Neurology* 62(7) 1233-1234 (2004).
MacKinnon et al., "Corticospinal Excitability Accompanying Ballistic Wrist Movements in Primary Dystonia," *Mov. Disord.* 19(3):273-284 (2004).
Mahowald et al., "Long Term Effects of Mira-Articular Botulinum Toxin A for Refractory Joint Pain," *Annual Meeting of the American College of Rheumatology* (Oct. 19, 2004).
Mannello et al., "Matrix Metalloproteinase Inhibitors as Anticancer Therapeutics," *Curr. Cancer Drug Targets* 5:285-298 (2005).
Maskos, K., "Crystal Structures of MMPs in Complex with Physiological and Pharmacological Inhibitors," *Biochimie* 87(3-4):249-263 (2005).
Mazo et al., "Botulinic Toxin in Patients with Neurogenic Dysfunction of the Lower Urinary Tracts," *Urologia* Jul.-Aug.:44-48 (2004).

Matteoli et al., "Synaptic Vesicle Endocytosis Mediates the Entry of Tetanus Neurotoxin Into Hippocampal Neurons," *Proc. Natl. Acad. Sci. USA* 93(23):13310-13315 (1996).
Montecucco, C., "How Do Tetanus and Botulinum Toxins Bind to Neuronal Membranes?" *Trends Biochem. Sci.* 11(8):314-317 (1986).
Montecucco et al., "SNARE Complexes and Neuroexocytosis: How Many, How Close?" *Trends Biochem. Sci.* 30(7):367-372 (2005).
Montecucco et al., "Structure and Function of Tetanus and Botulinum Neurotoxins," *Q. Rev. Biophys.* 28(4):423-472 (1995).
Mukherjee et al., "Endocytosis," *Physiol. Rev.* 77(3):759-803 (1997).
Namazi & Majd, "Botulinum Toxin as a Novel Addition to Anti-Arthritis Armamentarium," *Am. J. Immun.* 1(2):92-93 (2005).
Naumann & Jankovic, "Safety of Botulinum Toxin Type A: A Systematic Review and Meta-Analysis," *Curr. Med. Res. Opin.* 20(7):981-990 (2004).
Nishiki et al., "The High-Affinity Binding of *Clostridium botulinum* Type B Neurotoxin to Synaptotagmin II Associated with Gangliosides $G_{T1b}/G_{1a}$," *FEBS Lett.* 378(3):253-257 (1996).
Oost et al., "Design and Synthesis of Substrate-Based Inhibitors of Botulinum Neurotoxin Type B Metalloprotease," *Biopolymers* 71(6):602-619 (2003).
Özsoy et al., "Two-Plane Injection of Botulinum Exotoxin A in Glabellar Frown Lines," *Aesth. Plast. Surg.* 28(2):114-115 (2004).
Park & Simpson, "Inhalational Poisoning by Botulinum Toxin and inhalation Vaccination with Its Ilavy-Chain Component," *Infect. Immun.* 71(3):1147-1154 (2003).
Pidcock, F.S., "The Emerging Role of Therapeutic Botulinum Toxin in the Treatment of Cerebral Palsy," *J. Pediatr.* 145(2 Suppl):S33-S35 (2004).
Pless et al., "High-Affinity, Protective Antibodies to the Binding Domain of Botulinum Neurotoxin Type A," Infect. Immun. 69(1):570-574 (2001).
Porta et al., "Treatment of Phonic Tics in Patients with Tourette's Syndrome Using Botulinum Toxin Type A," *Neurol. Sci.* 24(6):420-423 (2003).
Prinz et al., "The Role of the Thioredoxin and Glutaredoxin Pathways in Reducing Protein Disulfide Bonds in the *Escherichia coli* Cytoplasm," *J. Biol. Chem.* 272(25):15661-15667(1997).
Pucinelli et al., "Botulinic Toxin for the Rehabilitation of Osteoarthritis Fixed-Flexion Knee Deformity," *Annual Meeting of the Osteoarthitis Research Society International*, pp. S143, Abstract P346 (2004).
Rajkumar & Conn, "Botulinum Toxin: A New Dimension in the Treatment of Lower Urinary Tract Dysfunction," *Urology* 64(1):2-8 (2004).
Reitz & Schurch, "Intravesical Therapy Options for Neurogenic Detrusor Overactivity," *Spinal Cord* 42(5):267-272 (2004).
Rigoni et al., "Site-Directed Mutagenesis Identifies Active-Site Residues of the Light Chain of Botulinum Neurotoxin Type A," *Biochem. Biophys. Res. Commun.* 288(5):1231-1237 (2001).
Rossetto et al., "SNARE Motif and Neurotoxins," *Nature* 372(6505):415-416 (1994).
Rummel et al., "The $H_{cc}$-Domain of Botulinum Neurotoxins A and B Exhibits a Singular Ganglioside Binding Site Displaying Serotype Specific Carbohydrate Interaction," *Mol. Microbiol.* 51(3):631-643 (2004).
Rummel et al., "Synaptotagmins I and II Act as Nerve Cell Receptors for Botulinum Neurotoxin G," *J. Biol. Chem.* 279(29):30865-30870 (2004).
Russman et al., "Cerebral Palsy: A Rational Approach to a Treatment Protocol, and the Role of Botulinum Toxin in Treatment," *Muscle Nerve* 20(Suppl 6):S181-S193 (1997).
Sadick & Matarasso, "Comparison of Botulinum Toxins A and B in the Treatment of Facial Rhytidcs," *Dermatol. Clin.* 22(2):221-226 (2004).
Salmanpoor & Rahmanian, "Treatment of Axillary Hyperhidrosis with Botulinum-A Toxin," *Int. J. Dermatol.* 41(7):428-430 (2002).
Sampaio et al., "Clinical Comparability of Marketed Formulations of Botulinum Toxin," *Mov. Disord.* 19(Suppl 8):S129-S136 (2004).
Schmulson & Valdovinos, "Current and Future Treatment of Chest Pain of Presumed Esophageal Origin," *Gastroenierol Clin. North Am.* 33(1):93-105 (2004).

(56) References Cited

OTHER PUBLICATIONS

Schurch, "The Role of Botulinum Toxin in Neurology," *Drugs of Today* 40(3):205-212 (2004).
Segelke et al., "Crystal Structure of *Clostridium botulinum* Neurotoxin Protease in a Product-Bound State: Evidence for Noncanonical Zinc Protease Activity," *Proc. Natl. Acad. Sci. USA* 101(18):6888-6893 (2004).
Shapiro et al., "Identification of a Ganglioside Recognition Domain of Tetanus Toxin Using a Novel Ganglioside Photoaffinity Ligand," *J. Biol. Chem.* 272(48):30380-30386 (1997).
Simpson, L.L., "Identification of the Major Steps in Botulinum Toxin Action," *Annu. Rev. Pharmacol. Toxicol.* 44:167-193 (2004).
Sukonpan et al., "Synthesis of Substrates and Inhibitors of Botulinum Neurotoxin Type A Metalloprotease," *J. Pept. Res.* 63(2):181-193 (2004).
Sutton et al., "Crystal Structure of a SNARE Complex Involved in Synaptic Exocytosis at 2.4 Å Resolution," *Nature* 395(6700):347-353 (1998).
Swaminathan & Eswaramoorthy, "Structural Analysis of the Catalytic and Binding Sites of *Clostridium botulinum* Neurotoxin B," *Nat. Struct. Biol.* 7(8):693-699 (2000).
Van Heyningen & Miller, "The Fixation of Tetanus Toxin by Ganglioside," *J. Gen. Microbiol.* 24:107-119 (1961).
Vartanian & Dayan, "Facial Rejuvenation Using Botulinum Toxin A: Review and Updates," *Facial Plast. Surg.* 20(1):11-19 (2004).
Wessel & Entner, "Botulinum Toxin Typ A in der Bellandlung der Adduktorenspastizität (Botulinum Toxin Treatment of Hip Adductor Spasticity in Multiple Sclerosis)," *Wien. Klin. Wochesnchr.* 113[Suppl 4]:20-24 (2001).
No Author, "Botulinum Toxin (*Botox*) for Axillary Hyperhidrosis," *Med. Lett. Drugs Ther.* 46(1191):76 (2004).
Marvaud et al., "Le Botulisme: Agent, Mode D'action des Neurotoxines Botuliques, Formes D'Acquisition, Traitement et Prevention," C.R. Biologies 325:863-878 (2002) (with English abstract).
Baldwin et al., "The C-Terminus of Botulinum Neurotoxin Type A Light Chain Contributes to Solubility, Catalysis, and Stability," Protein Expression and Purification 37:187-195 (2004).
Prabakaran et al., "Botulinum Neurotoxin Types B and E: Purification, Limited Proteolysis by Endoproteinase Glu-C and Pepsin, and Comparison of their Identified Cleaved Sites Relative to the Three-Dimensional Structure of Type A Neurotoxin," Toxicon 39:1515-1531 (2001).
Shone et al., "Inactivation of Clostridum Botulinum Type A Neurotoxin by Trypsin and Purification of Two Tryptic Fragments," European J. of Biochem. 151:75-82 (1985).
Allet et al., "A Bacterial Signal Peptide Directs Efficient Secretion of Eukaryotic Proteins in the Baculovirus Expression System," Pro. Exp. Pur. 9:61-68 (1997).
Cooke et al., "A Modified Escherichia coli Protein Production Strain Expressing Staphylococcal Nuclease, Capable of Auto-Hydrolysing Host Nucleic Acid," J. Biotech. 101:229-239 (2003).
Agarwal et al., Cloning, High Level Expression, Purification, and Crystallization of the Full Length Clostridium botulinum Neurotoxin Type E Light Chain, Pro. Exp. Pur. 34:95-102 (2004).
Pellet et al., "Neuronal Targeting, Internalization, and Biological Activity of a Recombinant Atoxic Derivative of Botulinum Neurotoxin A.," BBRC 405(4):673-677 (2011).
Band et al., "Recombinant Derivatives of Botulinum Neurotoxin A Engineered for Trafficking Studies and Neuronal Delivery," Prot. Exp. Pur. 71:62-73 (2010).
Gunnar Von Heijne, "Signals for Protein targeting into and Across Membranes," Subcell. Biochem. 22:1-19 (1994).

\* cited by examiner

```
BoNT A  NNWDLFFSPSEDNFTNDLNKGEEITSDTNIEAAEENISLDLIQQYYLTFNFDNEPENISIENLSSDIIGQLELMPNIERFP
BoNT B  DNEDLFFIADKNSFSDDLSKNERIEYNTQSNYIENDFPINEL---ILDTDLISKIE-LPSENTESLTDFNV-DVPVVEKQP
BoNT C  KNTDLPEIGDISDVKTDIFLRKDINEETEVIYYPDNVSVDQV---ILSKNTSEHGQ-L--DLLYPSIDSESEILPG-ENQV
BoNT D  KNNRLPYVADKDSISQEIFENKIITDETNVQNYSDNFSLDES---ILDGQVFINPEIV--DPLLPNVNMEPLNLPG-EEIV
BoNT E  NNGELFFVASENSYNDDNINTPKEIDDTVTSNNNYENDLDQV---ILNFNSESAPG-LSDEKLNLTIQND-AYIPKYDSNG
BoNT F  NNRELFFVASESSYNENDINTPKEIDDTTNLNNNYRNNLDEV---ILDYNSETIPQ-ISNQTLNTLVQDD-SYVPRYDSNG
BoNT G  NNEDLFFIANKDSFSKDLAKAETIAYNTQNNTIENNFSIDQL---ILDNDLSSGID-LPNENTEPFTNFDDIDIPVYIKQS

BoNT A  NG--KKYELDKYTMFHYLRAQEFEHGKSRIALTNSVNEALLNPSRVYTFFSSDYVKKVNKATEAAMFLGWVEQLVYDFTDE
BoNT B  AI--KKIFTDENTIFQVLYSQTFPLDIRDISLTSSFDDALLFSNKVYSFFSMDYIKTANKVVEAGLFAGWVKQLVNDFVIE
BoNT C  FYDNRTQNVDYLNSYYYLESQKLSDNVEDFTFTRSIEEALDNSAKVYTYFPT-LANKVNAGVQGGLFLMWANDVVEDFTTN
BoNT D  FYDDITKYVDYLNSYYYLESQKLSNNVENITLTTSVEEALGYSNKIYTFLPS-LAEKVNKGVQAGLFLNWANEVVEDFTTN
BoNT E  TSDIEQHDVNELNVFFYLDAQKVPEGENNVNLTSSIDTALLEQPKIYTFFSSEFINNVNKPVQAALFVSWIQQVLVDFTTE
BoNT F  TSEIEEHNVVDLNVFFYLHAQKVPEGETNISLTSSIDTALSEESQVYTFFSSEFINTINKPVHAALFISWINQVIRDFTTE
BoNT G  AL--KKIFVDGDSLFEYLHAQTFPSNIENLQLTNSLNDALRNNNKVYTFFSTNLVEKANTVVGASLFVNTVKGVIDDFTSE

BoNT A  TSEVSTTDKIADITIIIPYIGPALNIGNMLYKDDFVGALIFSGAVILLEFIPEIAIPVLGTFALVSYI---ANKVLTVQTI
BoNT B  ANKSNWMDKIADISLIVPYIGLALNVGNETAKGNFENAFEIAGASILLEFIPELLIPVVGAFLLESYI---DNKNKIIKTI
BoNT C  ILRKDTLDKISDVSAIIPYIGPALNISNSVRRGNFTEAFAVTGVTILLEAFPEFTIPALGAFVIYSKV---QERNEIIKTI
BoNT D  IMKKDTLDKISDVSVIIPYIGPALNIGNSALRGNFKQAFATAGVAFLLEGFPEFTIPALGVFTFYSST---QEREKIIKTI
BoNT E  ANQKSTVDKIADISIVVPYIGLALNIGNEAQKGNFKDALELLGACILLEFEPELLIPTILVFTIKSFLGSSDNKNKVIKAI
BoNT F  ATQKSTFDKIADISLVVPYVGLALNIGNEVQKENFKEAFELLGACILLEFVPELLIPTILVFTIKSFLGSSENKNKIIKAI
BoNT G  STQKSTIDKVSDVSIIIPYIGPALNVGNETAKENFKNAFEIGGAAILMEFIPELIVPIVGFFTLESYVG---NKGHIIMTI

BoNT A  DNALSKRNEKTDEVYKYIVTNWLAKVNTQIDLIRKKMKEALENQAEATKAIINYQYNQYTEEEKNNINF---NIDDLSSKLN
BoNT B  DNALTKRNEKTSDMYGLIVAQWLSTVNIQFYTIKEGMYKALNYQAQALKEIIKYRYNIYSEKEKSNINI--DFNDINSKLN
BoNT C  DNCLEQRIKRWKDSYEWMMGTWLSRIITQFNNISYQMYDSLNYQAGAIKAKIDLEYKKYSGSDKENIKS--QVENLKNSLD
BoNT D  ENCLEQRVKRWKDSYQWVVSNWLSRITTQFNHINYQMYDSLSYQADAIKAKIDLEYKKYSGSDKENIKS--QVENLKNSLD
BoNT E  NNALKERDEKWKEVYSFIVSNWMTKINTQFNKRKEQMYQALQNQVNAIKTLIESKVNSYTLEEKNELTNKYDIKQIENELN
BoNT F  NNSLMEREIKWKEIYSWIVSNWLTRINIQFNKRKEQMYQALQNQVDAIKTVIEYKYNNYTSDERNRLESEYNINNIREELN
BoNT G  SNALKKRDQKWTDMYGLIVSQWLSTVNIQFVTIKERMYNALNQSQAIEKIIEDQYNRYSEEDKMNINI--DFNDIDFKLN

BoNT A  ESINKAMININKFLNQCSVSYLMNSMIPYGVKRLEDFDASLKDALLKYIYDNRGT-LIGQVDRLKDKVNNTLSTDIPFQLS
BoNT B  EGINQALDNINNEINGCSVSYLMKKMIPLAVEKLLDFDNTLKKNLLNYIDENKLY-LIGSAEYEKSKVNKYLKTIMPFDLS
BoNT C  VKISEAMNNINKFIRECSVTYLFKNMLPKVIDELNEFDRNTKAKLINLID-SHNIILVGEVDRLKAKVNNSFQNTIPFNIF
BoNT D  VKISEAMNNINKFIRECSVTYLFKNMLPKVIDELNKFDLRTKTELINLID-SHNIILVGEVDRLKAKVNESFENTMPFNIF
BoNT E  QKVSIAMNNIDRFLTESSISYLMKLINEVKINKLREYDENVKTYLINYIIQHGSI-LGESQQELNSMVTDTINNSIPFKLS
BoNT F  KKVSLAMENIERFITESSIFYLMKLINEAKVSKLREYDEGVKEYLLDYISEHRSI-LGNSVQELNDLVTSTINNSIPFELS
BoNT G  QSINLAINNIDDFINQCSISYLMNRMIPLAVKKLKDFDDNLKRDLLEYIDTNELY-LLDEVNILKSKVNRHLKDSIPFDLS

Receptor Binding Domain →

BoNT A  KYVDNQRLLSTFTEVIKNTINTSILNLRYESNHLIDLSRYASKINIGSKVNFDPIDKNQIQLFN--LESSKIEVILKNAIV
BoNT B  IYTNDTILIEMFNKYNSEILNNIILNLRYKDNNLIDLSGYGAKVEVYDGVELN--DKNQFKLTSSAN--SKIRVTQNQNII
BoNT C  SYINNSLLKDIINEYFNNINDSKILSLQNRKNTLVDTSGYNAEVSEEGDVQLNPIFPFDFKLGSSGEDRGKVIVTQNENIV
BoNT D  SYINNSLLKDIINEYFNSINDSKILSLQNKKNALVDTSGYNAEVRVGDNVQLNTIYTNDFKLSSSGD---KIIVNLNNNIL
BoNT E  SYTDDKLLISYFNKFFKRIKSSSVLNMRYKNDKYVDTSGYDSNININGDVYKYPTNKNQFGIYN--DKLSEVNISQNDYII
BoNT F  SYTNDKIILYFNKLYKKIKDNSILDMRYENNKFIDISGYGSNISINGDVYIYSTNRNQFGIYSS--KPSEVNIAQNNDII
BoNT G  LYTKDTLLIQVFNNYISNISSNALLSLSYRGGRLIDSSGYGATMNVGSDVIFNDIGNGQFKLNNSEN--SNITAHQSKFVV
```

FIG. 1C

```
BoNT A  YNSMYENFSTSFWIRIPKYFNSISL---NNEYTIINCMENN-SGWKVSLNYGEIIWTLQDTQEIKQRVVFKVSQMINISDY
BoNT B  FNSVFLDFSVSFWIRIPKYRNDGIQNVIHNEYTIINCMKNN-SGWKISIRGNRIIWTLIDINGKTKSVFFEVNIREDISEY
BoNT C  YNSMYESFSISFWIRINK-WVSNLP-----GYTIIDSVKNN-SGWSIGIISNFLVFTLKQNEDSEQSINFSVDISNNAPGY
BoNT D  YSAIVENSSVSFWIKISKDLTNSH----NEYTIINSIEQN-SGWKLCIRNGNIETILQDVNRKYKSLIFDVSESLSHTGY
BoNT E  YDNKYKNFSISFWVRIPNYDNKIVN--VNNEYTIINCMRDNNSGWKVSLNHNEIIWTLQDNAGINQKLAFNVGNANGISDY
BoNT F  YNGRYQNFSISFWVRIPKYFNKVNL---NNEYTIIDCIRNNNSGWKISLNYNKIIWTLQDTAGNNQKLVFNVTQMISISDY
BoNT G  YDSMFDMFSINFWVRTPKYNNNDIQTVLQMEYTIISCIKND-SGWKVSIKGNRIIWTLIDVNAKSKSIFFEVSIKDNISDY

BoNT A  INRVLFVTITNNRLVNSKIYINGRLIDQKPISNLGNIHASNNIMFKLDGCRDT--------HRYIWIKYFNLFDKELNEKE
BoNT B  INRWFFVTITNN-LNNAKIYINGKLESNTDIKDIREVIANGEIIFKLDGDIDRT--------QFIWLKYFSIFNTELSQSN
BoNT C  -NKWFFVTVTNNMMGNMKIYINGKLIDTIKVKEITGINFSKTITFEINKIPDTGLITSDSDNINMWIRDFYIFAKELDGKD
BoNT D  TNKWFFVTITNNIMGYMKLYINGELKQSQKIEDIDEVKLDKTIVFGIDENIDE--------HQMLWIRDFNIFSKELSNED
BoNT E  INKWIFVTITNDRLGDSKLYINGNLIDQKSIINLGNIHVSDNILFKIVNCSYT--------RYIGIRYFNIFDKELDETE
BoNT F  INKWIFVTITNNRLGNSRIYINGNLIDEKSISNLGDIHVSDNILFKIVGCNDT--------RYVGIRYFKVFDTELGKTE
BoNT G  INKNFSITITNDRLGNANIYINGSLKKSEKIINLDRINSSNDIDFKLINCTDT--------TKFVWIKDFNIFGRELNATE

BoNT A  IKDLYDNQSNSGILKDFWGDYLQYDKPYYMLNLYDPNKYVDVNNVGIRGYMYLKGPR-GSVMTIN-IVLNSS-----LVRG
BoNT B  IEERYKIQSYSEYLKDFWGNPLMYNKEYYMFNAGNKNSYIKLKKDSPVG-EILT-RSKYNQNSK-MINYRD---LYIG
BoNT C  INILFNSLQYTNVVKDYWGNDLRYNKEYYMVNI----DYLNR-------YMYANS-RQIVFNTRR----NNND---FNEG
BoNT D  INIVVEGQILRNVIKDYWGNPLKFDTEYYIIND----MYIDR-------YIAPE-SNVLVLVR-YPDRSK----LYTG
BoNT E  IQTLYSNEPNTNILKDFWGNYLLYDKEYYLLNVLKPNNFIDRRKDSTL---SINNIRSTILLANR-------LYSG
BoNT F  IETLYSDEPDPSILKDFWGNYLLYNKRYYLLNLLRTDKSITQNSN----FLNINQQR-GVYQKPN-IFSNTR-----LYTG
BoNT G  VSSLYWIQSSTNTLKDFWGNPLRYDTQYYLFNQGMQNIYIK--------YFSKASMGET---APRTNFNNAAINYQNLYLG

BoNT A  TKFIIKKYASGN----KDNIVRNNDRVYINV-VVKNKEYRL-----ATNASQAGV----EKILSALEIPDVGNLS-----QV
BoNT B  EKFIIRRKSNSQSI-NDDIVRKEDYIYLDF-FNLNQEWRV-------YTYKYFK-KEEEKLFLAPISDSDEFYNTI---QI
BoNT C  YKIIIKRIRGNT----NDTRVRGGDILYFDM-TINNKAYNLFMKNE-TMYADNHST----EDIYAIGLRE-----------QT
BoNT D  NPITIKSVSDKNP---YSRILNGDNIILHM-LYNSRKYMIIRDTDIIYATQGG----ECSQNCVYALKL----------QS
BoNT E  IKVKIQRVNNSST--NDNLVRKNDQVYINFVASKTHLFPI-------YADTATTNK-EKTIKISSSGNRFN-------QV
BoNT F  VEVIIRKNGSTDISNIDNFVRKNDLAYINV-VDRDVEYRL-------YADIS-IAKP-EKIIKLIRTSNSNNSLG----QI
BoNT G  LRFIIKKASNSRNINNDNIVREGDYIYLNIDNISDESYRV-------YVLVNS--K-EIQTQLFLAPINDDPTFYDVLQI

BoNT A  VVMK--------SKNDQGITNKCKMNL---------QDNNGND-IGFIGFHQFNNI----------AKLVASNWYNRQI--ERS
BoNT B  KEYD-----------EQPTYSC--QLL---FKK-DFESTDEIGLIGIHRFYESGI-VFEEYKDYFCISKWYLK----EVK
BoNT C  KDINDNIIFQIQPMNNTYYYAS--QIFKSNFN--GFN----ISGICSIG-----------TYRFRLGGDKY-RHNVLVPT
BoNT D  NLGNYGIGIFSIKNIVSKNKYC-SQIF-SSFR----FN----TMILADI---------YKPWRFSFKNA---YT------PV
BoNT E  VVMN-----------SVGNNIVN----FKNNNGNIN----IGLLGFKA------------DTVVASTWY----YTHMR
BoNT F  IVMD------------SIGNNIVN----FQNNNGGN----IGLLGFHS-----------NNLVASSWY----YNNIR
BoNT G  KKYY-----------EKTTYNC--QILC--------EKDTKTFGLFGIGKFVKDYGYVWDTYDNYFCISQWYLRRISENIN

BoNT A  SRT---------LGCSWEFIPVDDGWGERPL
BoNT B  RKPYNLK------LGCNWQFIPKDEGWTE
BoNT C  VKQGNYASLTESTSTHWGFVPVSE
BoNT D  AVINYETKLI-STSSFWKFISRDPGWVE
BoNT E  DHIN--------SNGCFWNFISEEHGWQEK
BoNT F  KNIS--------SNGCFWSFISKEHGWQEN
BoNT G  KLR---------LGCNWQFIPVDEGWTE
```

TREATMENT METHODS USING ATOXIC NEUROTOXIN DERIVATIVES

This application claims the benefit of U.S. Provisional Patent Application Ser. No. 61/757,478, filed Jan. 28, 2013, which is hereby incorporated by reference in its entirety.

The subject matter of this application was made with support from the United States Government under National Institutes of Health grant R01 AI093504. The United States Government has certain rights.

FIELD OF THE INVENTION

This invention relates to treatment methods using atoxic neurotoxin derivatives.

BACKGROUND OF THE INVENTION

The Clostridial neurotoxins are a family of structurally similar proteins that target the neuronal machinery for synaptic vesicle exocytosis. Produced by anaerobic bacteria of the *Clostridium* genus, botulinum neurotoxins ("BoNT"s, seven immunologically distinct subtypes, A-G) and Tetanus neurotoxin ("TeNT") are the most poisonous substances known on a per-weight basis, with an $LD_{50}$ in the range of 0.5-2.5 ng/kg when administered by intravenous or intramuscular routes (*National Institute of Occupational Safety and Health*, "Registry of Toxic Effects of Chemical Substances (R-TECS)," Cincinnati, Ohio: National Institute of Occupational Safety and Health (1996)). BoNTs target cholinergic nerves at their neuromuscular junction, inhibiting acetylcholine release and causing peripheral neuromuscular blockade (Simpson, "Identification of the Major Steps in *Botulinum* Toxin Action," *Annu. Rev. Pharmacol. Toxicol.* 44:167-193 (2004)).

A genetic engineering platform that enables rational design of therapeutic agents based on Clostridial toxin genes was described in U.S. Pat. No. 7,785,606 to Ichtchenko and Band. The genetic engineering scheme was based on a two-step approach. Gene constructs, expression systems, and purification schemes were designed that produce physiologically active, recombinant Clostridial neurotoxin derivatives. The recombinant toxin derivatives retained structural features important for developing therapeutic candidates, or useful biologic reagents. Using the genetic constructs and expression systems developed by this paradigm, selective point mutations were then introduced to create recombinant atoxic Clostridial neurotoxin derivatives.

Treatment methods that involve contacting a patient with isolated, physiologically active, toxic, Clostridial neurotoxin derivatives have been described in U.S. Pat. No. 7,785,606 to Band and Ichtchenko. Also, isolated, physiologically active, toxic and atoxic *Clostridium botulinum* neurotoxin derivatives that have an S6 peptide sequence fused to the N-terminus of the proteins to enable site-specific attachment of cargo using Sfp phosphopantetheinyl transferase have been described as suitable for treatment (U.S. Patent Application Publication No. 2011/0206616 to Ichtchenko and Band). However, methods that involve treatment with an atoxic derivative of a Clostridial neurotoxin lacking a cargo attachment sequence at its N-terminus, and having a much higher $LD_{50}$ than a toxic derivative of a Clostridial neurotoxin or a wild type Clostridial neurotoxin, have not been described.

The present invention is directed to overcoming this and other limitations in the art.

SUMMARY OF THE INVENTION

The present invention relates to a treatment method. This method involves contacting a subject with an isolated, physiologically active, atoxic derivative of a Clostridial neurotoxin, said contacting being carried out to treat the subject, with the proviso that the neurotoxin derivative does not possess a cargo attachment peptide sequence at its N-terminus.

Genetic constructs and expression systems described herein are shown to produce a family of recombinant BoNT derivatives, with conformational and trafficking properties similar to the wild type BoNT toxins. These derivatives of Clostridial neurotoxins can be produced in toxic forms, having a toxicity comparable to that of the wild type toxin, or with mutations that reduce the metalloprotease activity responsible for toxicity (i.e., atoxic derivatives). The $LD_{50}$ of the atoxic neurotoxin derivatives is much higher than that of the wild type toxin.

As described herein, the atoxic neurotoxin derivatives (see U.S. Pat. No. 7,785,606 to Ichtchenko et al., which is hereby incorporated by reference in its entirety) unexpectedly have in vivo activity similar to the wild type neurotoxins used for pharmaceutical purposes. Yet, atoxic neurotoxin derivatives described herein offer significant treatment benefits over current pharmaceutical preparations of wild type neurotoxins produced from cultures. In particular, the atoxic derivatives described herein are safer, providing distinct advantages for medical uses and production/manufacturing. The improved therapeutic index will enable application to conditions where the toxicity of wild type neurotoxins limit their use because of safety concerns.

BRIEF DESCRIPTION OF THE DRAWINGS

FIGS. 1A-C are a comparative alignment of amino acid sequences of seven wild type *botulinum* neurotoxin serotypes, including *Clostridium botulinum* serotype A (wt BoNT A) (SEQ ID NO:1), *Clostridium botulinum* serotype B (wt BoNT B) (SEQ ID NO:2), *Clostridium botulinum* serotype C (wt BoNT C) (SEQ ID NO:3), *Clostridium botulinum* serotype D (wt BoNT D) (SEQ ID NO:4), *Clostridium botulinum* serotype E (wt BoNT E) (SEQ ID NO:5), *Clostridium botulinum* serotype F (wt BoNT F) (SEQ ID NO:6), and *Clostridium botulinum* serotype G (wt BoNT G) (SEQ ID NO:7). Gaps have been introduced to maximize homology. Amino acids identical in ≥50% of compared sequences are shown in black boxes. Amino acids constituting the active site of the catalytic domain of metalloprotease are marked by stars. Disulfide bridge between neurotoxin cysteine residues of the light and heavy chain are shown as a long horizontal bracket. The amino acid residues constituting the minimal catalytic domain of the light chain are hatched. The first amino acid of the C-terminal part of the protein heavy chain (N872 for BoNT A), is shown with a white arrow, as is the first amino acid considered to constitute the receptor-binding domain. Amino acids absent in the mature dichain BoNT A molecule along with the aligned amino acids of the other BoNT serotypes are boxed. A white arrow is also positioned at the first amino acid of the neurotoxins' light chain.

DETAILED DESCRIPTION OF THE INVENTION

Figure 2:
FIG. 2 is a photograph showing the results of in vivo studies performed by intramuscular injection into the lateral gastrocnemius with 0.5 µg/mouse of BoNT A/ad-0 (experimental) in 3 µA of 0.9% NaCl or by injecting 3 µA of 0.9% of NaCl without BoNT A/ad-0 (control). Muscle paralysis and digital abduction was recorded 48 hours after. The two upper panel photographs show control mice, with the arrow in the upper right photograph indicating the site of injection. The three lower panel photographs show experimental mice. Digital abduction muscle paralysis was only observed in mice injected with BoNT A/ad-0. Experimental, n=10. Control, n=5. Representative results are shown in the photographs in the three bottom panels.

The present invention relates to a treatment method. This method involves contacting a subject with an isolated, physiologically active, atoxic derivative of a Clostridial neurotoxin, said contacting being carried out to treat the subject, with the proviso that the neurotoxin derivative does not possess a cargo attachment peptide sequence at its N-terminus.

According to one embodiment, the derivative of a Clostridial neurotoxin of the present invention is a derivative of a *Clostridium botulinum* neurotoxin. *Clostridium botulinum* has multiple serotypes (A-G). Suitable derivatives of a Clostridial neurotoxin may be derivatives of any of the *Clostridium botulinum* serotypes. In addition, suitable derivatives of a Clostridial neurotoxin of the present invention may be derivatives of more than one *Clostridium botulinum* serotype. For example, it may be desirable to have a derivative of a Clostridial neurotoxin constructed of a light chain (LC) region from one *Clostridium botulinum* serotype (e.g., serotype A, BoNT A) and a heavy chain (HC) region from another *Clostridium botulinum* serotype (e.g., serotype B, BoNT B). Also, suitable derivatives of a Clostridial neurotoxin of the present invention include chimeras using other receptor ligands, e.g., epidermal growth factor ("EGF") for LC delivery to cancer cells (see U.S. Patent Application Publication no. 2012/0064059 to Foster et al., which is hereby incorporated by reference in its entirety).

By "derivative" it is meant that the Clostridial neurotoxin is substantially similar to the wild type toxin, but has been modified slightly as described herein. For example, derivatives include Clostridial neurotoxins that are at least 60%, 70%, 80%, 85%, 90%, 95%, 96%, 97%, 98%, or 99% identical to a wild type neurotoxin.

Isolated derivatives of a Clostridial neurotoxin are physiologically active. This physiological activity includes, but is not limited to, toxin immunogenicity, trans- and intra-cellular trafficking, cell recognition and targeting, and paralytic activity. In one embodiment, the derivative of a Clostridal neurotoxin is a derivative of a full-length Clostridial neurotoxin.

The atoxic derivative of a Clostridial neurotoxin designated herein using the "ad-0" designation, does not have an S6 peptide sequence fused to the N-terminus of the neurotoxin derivative, as described in U.S. Patent Application Publication No. 2011/0206616 to Icthtchenko and Band, which is hereby incorporated by reference in its entirety.

Figure 1A:
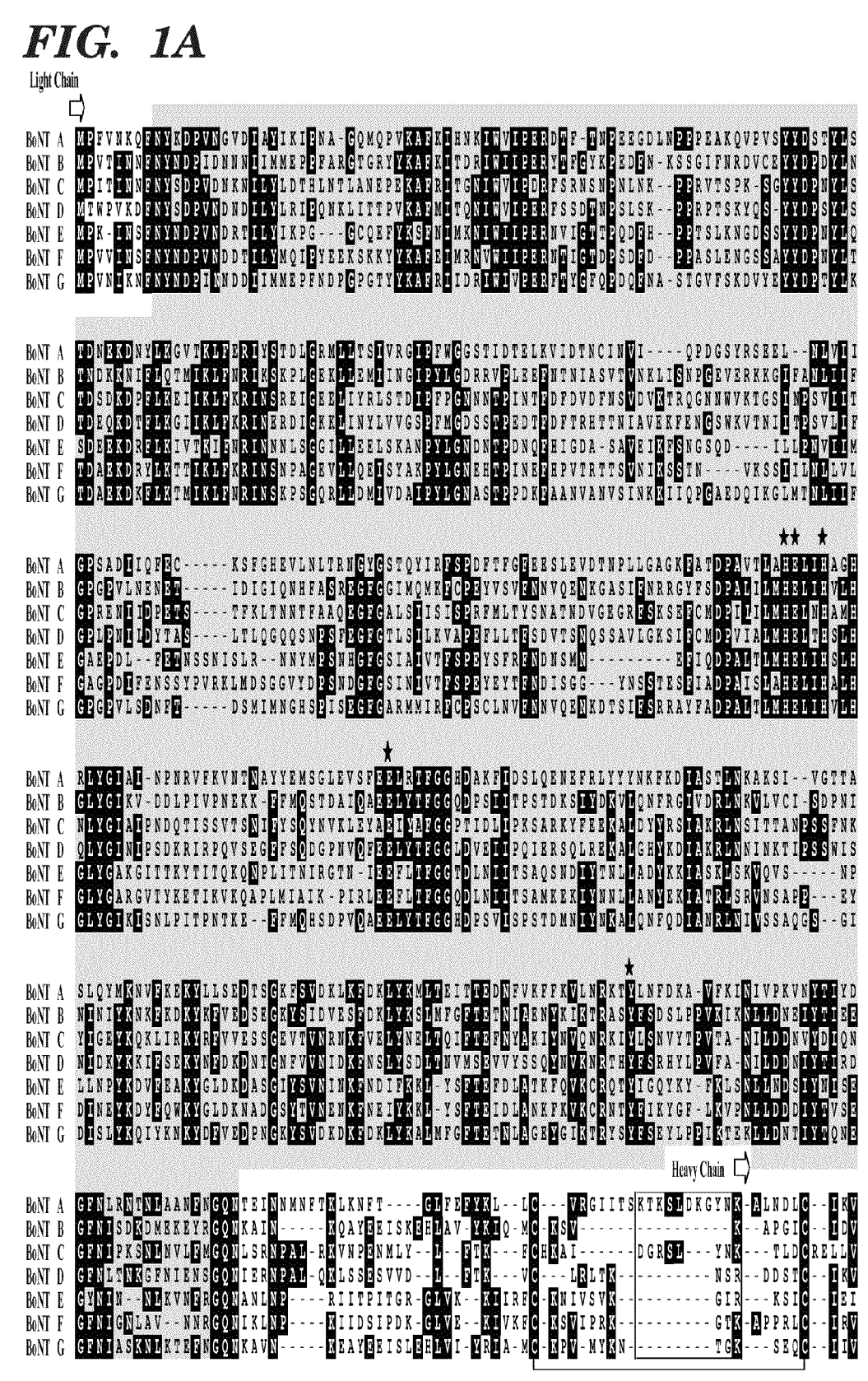

The mechanism of cellular binding and internalization of Clostridial neurotoxins is still not completely understood. The C-terminal portion of the heavy chain of all Clostridial neurotoxins binds to gangliosides (sialic acid-containing glycolipids), with a preference for gangliosides of the $G_{1b}$ series (Montecucco et al., "Structure and Function of Tetanus and *Botulinum* Neurotoxins," *Q. Rev. Biophys.* 28:423-472 (1995); Montecucco, "How Do Tetanus and *Botulinum* Toxins Bind to Neuronal Membranes?" *TIBS* 11:314-317 (1986); and Van Heyningen et al., "The Fixation of Tetanus Toxin by Ganglioside," *J. Gen. Microbiol.* 24:107-119 (1961), which are hereby incorporated by reference in their entirety). The sequence responsible for ganglioside binding has been identified for the structurally similar TeNT molecule, and is located within the 34 C-terminal amino acid residues of its heavy chain. BoNT A, BoNT B, BoNT C, BoNT E, and BoNT F share a high degree of homology with TeNT in this region (FIG. 1) (Shapiro et al., "Identification of a Ganglioside Recognition Domain of Tetanus Toxin Using a Novel Ganglioside Photoaffinity Ligand," *J. Biol. Chem.* 272:30380-30386 (1997), which is hereby incorporated by reference in its entirety). Multiple types of evidence suggest the existence of at least one additional component involved in the binding of Clostridial neurotoxins to neuronal membranes (Montecucco et al., "Structure and Function of Tetanus and *Botulinum* Neurotoxins," *Q. Rev. Biophys.* 28:423-472 (1995); Montecucco, "How Do Tetanus and *Botulinum* Toxins Bind to Neuronal Membranes?" *TIBS* 11:314-317 (1986), which are hereby incorporated by reference in their entirety). In two reports (Nishiki et al., "The High-Affinity Binding of *Clostridium Botulinum* Type B Neurotoxin to Synaptotagmin II Associated with Gangliosides $G_{T1b}/G_{D1a}$," *FEBS Lett.* 378: 253-257 (1996); Dong et al., "Synaptotagmins I and II Mediate Entry of *Botulinum* Neurotoxin B into Cells," *J. Cell Biol.* 162:1293-1303 (2003), which are hereby incorporated by reference in their entirety), synaptotagmins were identified as possible candidates for the auxiliary BoNT B receptor, and synaptotagmins I and II were implicated as neuronal receptors for BoNT G (Rummel et al., "Synaptotagmins I and II Act as Nerve Cell Receptors for *Botulinum* Neurotoxin G," *J. Biol. Chem.* 279:30865-30870 (2004), which is hereby incorporated by reference in its entirety). Dong et al., "SV2 is the Protein Receptor for *Botulinum* Neurotoxin A," *Science* 312: 592-596 (2006), which is hereby incorporated by reference in its entirety, showed that BoNT A enters neurons by binding to the synaptic vesicle protein SV2 (isoforms A, B, and C). However, despite the structural similarity in the putative receptor-binding domain of Clostridial neurotoxins, other toxin subtypes show no affinity for SV2 and instead may target synaptotagmins or synaptotagmin-related molecules. Lipid rafts (Herreros et al., "Lipid Rafts Act as Specialized Domains for Tetanus Toxin Binding and Internalization into Neurons," *Mol. Biol. Cell* 12:2947-2960 (2001), which is hereby incorporated by reference in its entirety) have been implicated as a specialized domain involved in TeNT binding and internalization into neurons, but these domains are widely distributed on multiple cell types, and therefore cannot simply explain the high specificity of the toxins for neurons.

Clostridial neurotoxins are internalized through the presynaptic membrane by an energy-dependent mechanism (Montecucco et al., "Structure and Function of Tetanus and *Botulinum* Neurotoxins," *Q. Rev. Biophys.* 28:423-472 (1995); Matteoli et al., "Synaptic Vesicle Endocytosis Mediates the Entry of Tetanus Neurotoxin into Hippocampal Neurons," *Proc. Natl. Acad. Sci. USA* 93:13310-13315 (1996); and Mukherjee et al., "Endocytosis," *Physiol. Rev.* 77:759-803 (1997), which are hereby incorporated by reference in their entirety), and rapidly appear in vesicles where they are at least partially protected from degradation (Dolly et al., "Acceptors for *Botulinum* Neurotoxin Reside on Motor Nerve Terminals and Mediate Its Internalization," *Nature* 307:457-460 (1984); Critchley et al., "Fate of Tetanus Toxin Bound to the Surface of Primary Neurons in Culture: Evidence for Rapid Internalization," *J. Cell Biol.* 100:1499-1507 (1985), which are hereby incorporated by reference in their entirety). The BoNT complex of light and heavy chains interacts with the endocytic vesicle membrane in a chaperone-like way, preventing aggregation and facilitating translocation of the light chain in a fashion similar to the protein conducting/translocating channels of smooth ER, mitochondria, and chloroplasts (Koriazova et al., "Translocation of *Botulinum* Neurotoxin Light Chain Protease through the Heavy Chain Channel," *Nat. Struct. Biol.* 10:13-18 (2003), which is hereby incorporated by reference in its entirety). Acidification of the endosome is believed to induce pore formation, which allows translocation of the light chain to the cytosol upon reduction of the interchain disulfide bond (Hoch et al., "Channels Formed by *Botulinum*, Tetanus, and Diphtheria Toxins in Planar Lipid Bilayers: Relevance to Translocation of Proteins Across Membranes," *Proc. Natl. Acad. Sci. USA* 82:1692-1696 (1985), which is hereby incorporated by reference in its entirety). Within the cytosol, the light chain displays a zinc-endopeptidase activity specific for protein components of the synaptic vesicle exocytosis apparatus. TeNT and BoNT B, BoNT D, BoNT F, and BoNT G recognize VAMP/synaptobrevin. This integral protein of the synaptic vesicle membrane is cleaved at a single peptide bond, which differs for each neurotoxin. BoNT A, BoNT C, and BoNT E recognize and cleave SNAP-25, a protein of the presynaptic membrane, at different sites within the carboxyl terminus segment. BoNT C also cleaves syntaxin, another protein of the nerve terminal plasmalemma (Montecucco et al., "Structure and Function of Tetanus and *Botulinum* Neurotoxins," *Q. Rev. Biophys.* 28:423-472 (1995); Sutton et al., "Crystal Structure of a SNARE Complex Involved in Synaptic Exocytosis at 2.4 A Resolution," *Nature* 395:347-353 (1998), which are hereby incorporated by reference in their entirety). The cleavage of such components of the synaptic release machinery results in inhibition of acetylcholine release in motor neurons, ultimately leading to neuromuscular paralysis.

The isolated derivative of a Clostridial neurotoxin employed in the method of the present invention is physiologically active and atoxic. The endopeptidase activity responsible for Clostridial neurotoxin toxicity is believed to be associated with the presence of a HExxHxxH (SEQ ID NO:8) motif in the light chain, characteristic of metalloproteases (FIGS. 1A-C). Mutagenesis of BoNT A light chain, followed by microinjection of the corresponding mRNA into presynaptic cholinergic neurons of *Aplysia californica*, allowed the minimal essential domain responsible for toxicity to be identified (Kurazono et al., "Minimal Essential Domains Specifying Toxicity of the Light Chains of Tetanus Toxin and *Botulinum* Neurotoxin Type A," *J. Biol. Chem.* 267:14721-14729 (1992), which is hereby incorporated by reference in its entirety). Site-directed mutagenesis of BoNT A light chain pinpointed the amino acid residues involved in $Zn^{2+}$ coordination, and formation of the active metalloendoprotease core which cleaves SNAP-25 (Rigoni et al., "Site-Directed Mutagenesis Identifies Active-Site Residues of the Light Chain of *Botulinum* Neurotoxin Type A," *Biochem. Biophys. Res. Commun.* 288:1231-1237 (2001), which is hereby incorporated by reference in its entirety). The three-dimensional structures of Clostridial neurotoxins and their derivatives confirmed the mutagenesis results, and detailed the spatial organization of the protein domains. For the BoNT A holotoxin, crystal structure was obtained to a resolution of 3.3 Å (Lacy et al., "Crystal Structure of *Botulinum* Neurotoxin Type A and Implications for Toxicity," *Nat. Struct. Biol.* 5:898-902 (1998), which is hereby incorporated by reference in its entirety). The BoNT B holotoxin crystal structure was determined at 1.8 and 2.6 Å resolution (Swaminathan et al., "Structural Analysis of the Catalytic and Binding Sites of *Clostridium Botulinum* Neurotoxin B," *Nat. Struct. Biol.* 7:693-699 (2000), which is hereby incorporated by reference in its entirety). Recently, a crystal structure for BoNT E catalytic domain was determined to 2.1 Å resolution (Agarwal et al., "Structural Analysis of *Botulinum* Neurotoxin Type E Catalytic Domain and Its Mutant Glu212>Gln Reveals the Pivotal Role of the Glu212 Carboxylate in the Catalytic Pathway," *Biochemistry* 43:6637-6644 (2004), which is hereby incorporated by reference in its entirety). The later study provided multiple interesting structural details, and helps explain the complete loss of metalloendoproteolytic activity in the BoNT E LC E212>Q mutant. The availability of this detailed information on the relationship between the amino acid sequence and biological activities of Clostridial toxins enables the design of modified toxin genes with properties specifically altered for therapeutic goals.

Thus, in one embodiment, the physiologically active and atoxic derivative of a Clostridial neurotoxin has a metalloprotease disabling mutation. Specific metalloprotease disabling mutations are described in U.S. Pat. No. 7,785,606 to Ichthchenko and Band, which is hereby incorporated by reference in its entirety. Additional point mutations can be introduced to further modify the characteristics of the atoxic derivative, some of which are also described in U.S. Pat. No. 7,785,606 to Ichthchenko and Band, which is hereby incorporated by reference in its entirety.

The physiologically active and atoxic derivative of a Clostridial neurotoxin may also have a non-native motif (e.g., a SNARE motif) in the light chain region that is capable of inactivating light chain metalloprotease activity in a toxic Clostridial neurotoxin, or otherwise modifying the behavior of the derivative. The sequences of nine non-native motifs that may be substituted for alpha-helix domains are described in U.S. Pat. No. 7,785,606 to Ichtchenko and Band, which is hereby incorporated by reference in its entirety. Atoxic derivatives that incorporate sequences to target other cellular receptors are also possible (e.g., EGF or cancer cells) (see U.S. Patent Application Publication No. 2012/0064059 to Foster et al., which is hereby incorporated by reference in its entirety).

In one embodiment, the physiologically active and atoxic derivative of a Clostridial neurotoxin has an $LD_{50}$ that is at least 1,000; 2,000; 5,000; 7,000; 9,000; 10,000; 20,000; 30,000; 40,000; 50,000; 60,000; 70,000; 80,000; 90,000; 100,000; or 500,000-fold higher than the $LD_{50}$ of wild type Clostridial neurotoxin. The particular mode of administration may affect the $LD_{50}$ of the derivative of a Clostridial neurotoxin.

In one embodiment, the derivative of a Clostridal neurotoxin of the present invention is produced by cleaving a propeptide. The propeptide is cleaved at the highly specific protease cleavage site to form a light and heavy chain, with molecular weights of approximately 50 kD and 100 kD, respectively. The light and heavy chain regions are linked by a disulfide bond.

In one embodiment, the propeptide is contacted with a highly specific protease (e.g., enterokinase or TEV protease) under conditions effective to enable cleavage at the intermediate region of the propeptide of the present invention. Preferably, the expressed propeptide has one or more disulfide bridges.

As discussed infra, Clostridial neurotoxins and their derivatives described herein are synthesized as single chain propeptides which are later activated by a specific proteolysis cleavage event, generating a dimer joined by a disulfide bond. These structural features can be illustrated using BoNT A as an example, and are generally applicable to all *Clostridium botulinum* serotypes. The mature BoNT A is composed of three functional domains of Mr~50,000, where the catalytic function responsible for toxicity is confined to the light chain (residues 1-437), the translocation activity is associated with the N-terminal half of the heavy chain (residues 448-872), and cell binding is associated with its C-terminal half (residues 873-1,295) (Johnson, "Clostridial Toxins as Therapeutic Agents: Benefits of Nature's Most Toxic Proteins," *Annu. Rev. Microbiol.* 53:551-575 (1999); Montecucco et al., "Structure and Function of Tetanus and *Botulinum* Neurotoxins," *Q. Rev. Biophys.* 28:423-472 (1995), which are hereby incorporated by reference in their entirety).

Optimized expression and recovery of recombinant neurotoxins for BoNT serotypes in a native and physiologically active state is achieved by the introduction of one or more alterations to the nucleotide sequences encoding the BoNT propeptides, as discussed infra. These mutations are designed to maximize yield of recombinant derivatives of a Clostridial neurotoxin, while retaining the native toxins' structure and biological activity.

Common structural features of the wild-type *Clostridium botulinum* neurotoxin propeptides are shown in FIGS. 1A-C. These structural features are illustrated using wt BoNT A propeptide as an example, and are generalized among all *Clostridium botulinum* serotypes. wt BoNT A propeptide has two chains, a light chain ("LC") of Mr ~50,000 and a heavy chain ("HC") of Mr ~100,000, linked by a disulfide bond between $Cys_{429}$ and $Cys_{453}$. As illustrated in FIGS. 1A-C, all seven BoNT serotype propeptides have a light chain region and a heavy chain region linked by a disulfide bond. Two essential Cys residues, one adjacent to the C-terminus of the light chain, and a second adjacent to the N-terminus of the heavy chain are present in all seven BoNT serotypes. These two Cys residues form the single disulfide bond holding the HC and LC polypeptides together in the mature neurotoxin. This disulfide bond enables the mature neurotoxin to accomplish its native physiological activities by permitting the HC and LC to carry out their respective biological roles in concert. The disulfide bond between HC and LC polypeptides in all seven serotypes is illustrated in FIG. 1A by the solid line joining the involved Cys residues. The outlined box in FIG. 1A illustrates the intermediate region defined by amino acid residues $Lys_{438}$-$Lys_{448}$ of wt BoNT A. This intermediate region identifies the amino acids eliminated during maturation of wt BoNT A, and believed to be excised by a protease endogenous to the host microorganism. This cleavage event, described infra, generates the biologically active BoNT HC-LC dimer. The outlined amino acid residues in FIGS. 1A-C, representing amino acid residues approximately in the 420 to 450 range for all seven BoNT serotypes, can be considered as a region "non-essential" to the toxins' physiological activity and, therefore, represents targets for directed mutagenesis in all seven BoNT serotypes.

All seven wt BoNT serotypes referred to herein contain Lys or Arg residues in the intermediate region defined by the box in FIG. 1A, which make the propeptides susceptible to activation by trypsin. Native BoNT A propeptide recovered from young bacterial cultures can be activated by trypsinolysis, with production of intact, S—S bound light and heavy chain. Though multiple additional trypsin-susceptible sites are present in the propeptides, they are resistant to proteolysis due to their spatial positions within the native toxin molecule (Dekleva et al., "Nicking of Single Chain *Clostridium botulinum* Type A Neurotoxin by an Endogenous Protease," *Biochem. Biophys. Res. Commun.* 162:767-772 (1989); Lacy et al., "Crystal Structure of *Botulinum* Neurotoxin Type A and Implications for Toxicity," *Nat. Struct. Biol.* 5:898-902 (1998), which are hereby incorporated by reference in their entirety). A second site in the native propeptide of several BoNT serotypes can be susceptible to trypsin cleavage when subjected to higher enzyme concentrations or incubation times (Chaddock et al., "Expression and Purification of Catalytically Active, Non-Toxic Endopeptidase Derivatives of *Clostridium botulinum* Toxin Type A," *Protein Expr. Purif.* 25:219-228 (2002), which is hereby incorporated by reference in its entirety). This trypsin-susceptible site is located in the region adjacent to the toxin receptor binding domain. This region of the HC peptide is found to be exposed to solvent in BoNT serotypes for which information is available on their 3-D crystal structure (Lacy et al., "Crystal Structure of *Botulinum* Neurotoxin Type A and Implications for Toxicity," *Nat. Struct. Biol.* 5:898-902 (1998); Swaminathan et al., "Structural Analysis of the Catalytic and Binding Sites of *Clostridium botulinum* Neurotoxin B," *Nat. Struct. Biol.* 7:693-699 (2000), which are hereby incorporated by reference in their entirety).

In one embodiment, the propeptide has an intermediate region connecting the light and heavy chain regions which has a highly specific protease cleavage site and no low-specificity protease cleavage sites. For purposes of the present invention, a highly specific protease cleavage site has three or more specific adjacent amino acid residues that are recognized by the highly specific protease in order to permit cleavage (e.g., an enterokinase cleavage site or a TEV recognition sequence). In contrast, a low-specificity protease cleavage site has two or less adjacent amino acid residues that are recognized by a protease in order to enable cleavage (e.g., a trypsin cleavage site).

In all seven BoNT serotypes, the amino acid preceding the N-terminus of the heavy chain is a Lys or Arg residue which is susceptible to proteolysis with trypsin. This trypsin-susceptible site can be replaced with a five amino acid enterokinase cleavage site (i.e., DDDDK (SEQ ID NO:9)) upstream of the heavy chain's N-terminus. Alternatively, the trypsin-susceptible site can be replaced with a tobacco etch virus protease recognition ("TEV") sequence. Use of a TEV sequence enables a one-step heterodimer-forming cleavage event. See U.S. Patent Application Publication No. 2011/0206616 to Ichtchenko et al., which is hereby incorporated by reference in its entirety. Either of these modifications enables standardization activation with specific enzymes. In serotypes A and C, additional Lys residues within this region may be mutated to either Gln or His, thereby eliminating additional trypsin-susceptible sites. Trypsin-susceptible recognition sequences also occur upstream of the heavy chain's receptor-binding domain in serotypes A, E, and F. This region's susceptibility to proteolysis is consistent with its exposure to solvent in the toxin's 3-D structure, as shown by X-ray crystallography analysis. Therefore, in serotypes A, E, and F, the susceptible residues are modified to Asn. These modifications enable standardization activation with either enterokinase or TEV.

Signal peptides and N-terminal affinity tags are also preferably introduced, as required, to enable secretion and recovery and to eliminate truncated variants. The affinity tags can be separated from the N-terminus and C-terminus of the neurotoxin by cleavage using the same specific proteases used to cleave the heavy and light chain.

In one embodiment, the derivative of a Clostridial neurotoxin is from a propeptide that has a metalloprotease disabling mutation. The amino acid residues constituting the minimal catalytic domain of the light chain of the propeptide are illustrated in FIG. 1A by hatching. Specific amino acid residues constituting the active site of the catalytic domain of the metalloprotease are marked by stars in FIG. 1A.

A variety of Clostridial neurotoxin propeptides with light chain regions containing non-native motifs (e.g., SNARE motif peptides) in place of surface alpha-helix domains can be created. These non-native motif bearing propeptides are generated by altering the nucleotide sequences of nucleic acids encoding the propeptides.

In one embodiment, the light and heavy chains of the propeptide are not truncated.

In one embodiment, the propeptide further comprises a signal peptide coupled to the light chain region, where the signal peptide is suitable to permit secreation of the propeptide from a eukaryotic cell to a medium. Suitable signal peptides are described in U.S. Pat. No. 7,785,606 to Ichtchenko and Band, which is hereby incorporated by reference in its entirety. A suitable signal peptide is a gp64 signal peptide.

The propeptide may also have an affinity tag located between the signal peptide and the light chain region and/or at the C-terminus of the propeptide. A suitable affinity tag is the hexahistidine affinity tag MPMLSAIVLYVLLAAAAH-SAFAAMVHHHHHHSAS . . . (SEQ ID NO:10). Structural variations of suitable Clostridial neurotoxin propeptides that possess a cargo attachment peptide sequence are described in U.S. Patent Application Publication No. 2011/0206616 to Ichtchenko and Band, which is hereby incorporated by reference in its entirety. Propeptides that encode atoxic derivatives of a Clostridial neurotoxin suitable for use in the method of the present invention may have any of the structural features of the propeptides described in U.S. Patent Application Publication No. 2011/0206616 to Ichtchenko and Band, which is hereby incorporated by reference in its entirety, other than the cargo attachment peptide sequence at the N-terminus. As described in U.S. Patent Application Publication No. 2011/0206616 to Ichtchenko and Band, which is hereby incorporated by reference in its entirety, a single protease cleavage step can be used for activation and removal of affinity tags.

Isolated nucleic acid molecules that encode atoxic derivatives of a Clostridial neurotoxin suitable for use in the method of the present invention are described in U.S. Pat. No. 7,785,606 to Ichtchenko and Band, which is hereby incorporated by reference in its entirety.

In one embodiment, the nucleic acid molecule has a metalloprotease disabling mutation, as described supra.

In one embodiment, the derivative of a Clostridal neurotoxin is a recombinant protein. Expression systems having a nucleic acid molecule encoding an isolated, physiologically active, atoxic derivative of a Clostridial neurotoxin in a heterologous vector, and host cells having a heterologous nucleic acid molecule encoding an isolated, physiologically active, atoxic derivative of a Clostridial neurotoxin are described in U.S. Pat. No. 7,785,606 to Ichtchenko and Band, which is hereby incorporated by reference in its entirety.

Expressing a recombinant, physiologically active, atoxic derivative of a Clostridial neurotoxin is carried out by providing a nucleic acid construct having a nucleic acid molecule encoding a propeptide as described herein. The nucleic acid construct has a heterologous promoter operably linked to the nucleic acid molecule and a 3' regulatory region operably linked to the nucleic acid molecule. The nucleic acid construct is then introduced into a host cell under conditions effective to express the physiologically active, atoxic derivative of a Clostridial neurotoxin.

In one embodiment, the expressed neurotoxin derivative is contacted with a highly specific protease under conditions effective to effect cleavage at the intermediate region. Preferably, the intermediate region of the propeptide is not cleaved by proteases endogenous to the expression system or the host cell.

Expression of a derivative of a Clostridial neurotoxin can be carried out by introducing a nucleic acid molecule encoding a propeptide into an expression system of choice using conventional recombinant technology. Generally, this involves inserting the nucleic acid molecule into an expression system to which the molecule is heterologous (i.e., not normally present). The introduction of a particular foreign or native gene into a mammalian host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells.

Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted Clostridial neurotoxin propeptide-coding sequences.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pFastBac series (Invitrogen), pET series (see F. W. Studier et. al., "Use of T7 RNA Polymerase to Direct Expression of Cloned Genes," *Gene Expression Technology* Vol. 185 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, as described by Sambrook et al., *Molecular Cloning: A Laboratory Manual*, Cold Springs Laboratory, Cold Springs Harbor, N.Y. (1989), which is hereby incorporated by reference in its entirety.

A variety of host-vector systems may be utilized to express the propeptide-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression see Roberts and Lauer, *Methods in Enzymology* 68:473 (1979), which is hereby incorporated by reference in its entirety.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV 5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The nucleic acid, a promoter molecule of choice, a suitable 3' regulatory region, and if desired, a reporter gene, are incorporated into a vector-expression system of choice to prepare a nucleic acid construct using standard cloning procedures known in the art, such as described by Sambrook et al., *Molecular Cloning: A Laboratory Manual*, Third Edition, Cold Spring Harbor: Cold Spring Harbor Laboratory Press, New York (2001), which is hereby incorporated by reference in its entirety.

The nucleic acid molecule encoding a derivative of a Clostridial neurotoxin is inserted into a vector in the sense (i.e., 5'→3') direction, such that the open reading frame is properly oriented for the expression of the encoded propeptide under the control of a promoter of choice. Single or multiple nucleic acids may be ligated into an appropriate vector in this way, under the control of a suitable promoter, to prepare a nucleic acid construct.

Once the isolated nucleic acid molecule encoding the propeptide has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like. Preferable host cells of the present invention include, but are not limited to, *Escherichia coli*, insect cells, and *Pichia pastoris* cells.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

In carrying out the method of the present invention, contacting a subject with the isolated, physiologically active, atoxic derivative of a Clostridal neurotoxin can be carried out by administering the isolated derivative of a Clostridial neurotoxin to a subject inhalationally, parenterally, for example, subcutaneously, intravenously, intramuscularly, intraperitoneally, by intranasal instillation, or by application to mucous membranes, such as, that of the nose, throat, and bronchial tubes. The neurotoxin derivative may be administered alone or with suitable pharmaceutical carriers, and can be in solid or liquid form such as, tablets, capsules, powders, solutions, suspensions, or emulsions.

The neurotoxin derivative may be orally administered, for example, with an inert diluent, or with an assimilable edible carrier, or may be enclosed in hard or soft shell capsules, or may be compressed into tablets, or may be incorporated directly with the food of the diet. For oral therapeutic administration, the neurotoxin derivative may be incorporated with excipients and used in the form of tablets, capsules, elixirs, suspensions, syrups, and the like. In one embodiment, the formulation includes hemagglutinin proteins similar to those produced by *Clostridium* species to protect the neurotoxin in the gastrointestinal tract. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it may contain, in addition to materials of the above type, a liquid carrier, such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The neurotoxin derivative may also be administered parenterally. Solutions or suspensions can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that syringability is possible. It must be stable under the conditions of manufacture and storage and can be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), vegetable oils, hyaluronic acid, and suitable mixtures thereof.

The neurotoxin derivative may also be administered directly to the airways in the form of an aerosol. For use as aerosols, the neurotoxin derivative in solution or suspension may be packaged in a pressurized aerosol container together with suitable propellants, for example, hydrocarbon propellants like propane, butane, or isobutane with conventional adjuvants. The neurotoxin derivative also may be administered in a non-pressurized form such as in a nebulizer or atomizer.

BoNTs pass across epithelial surfaces without being destroyed or causing local toxicity. Passage across epithelia is believed to occur by specific binding and transcytosis. The ability of intact BoNT A to pass though pulmonary epithelia and resist proteolytic inactivation was demonstrated in rat primary alveolar epithelial cells and in immortalized human pulmonary adenocarcinoma (Calu-3) cells. The rate of transport was greater in the apical-to-basolateral direction than in the basolateral-to-apical direction, and it was blocked by serotype-specific toxin antibodies (Park et al., "Inhalational Poisoning by *Botulinum* Toxin and Inhalation Vaccination with Its Heavy-Chain Component," *Infect. Immun.* 71:1147-1154 (2003), which is hereby incorporated by reference in its entirety).

Targeting the CNS may require intra-thecal or intra-ventricular administration. Administration may occur directly to the CNS. Alternatively, administration to the CNS may involve retrograde transport from peripheral neurons (motor neurons, nociceptors) to spinal ganglia (see Caleo et al., "A Reappraisal of the Central Effects of *Botulinum* Neurotoxin Type A: By What Mechanism?" *Journal of Neurochemistry* 109:15-24 (2009), which is hereby incorporated by reference in its entirety).

Derivatives of a Clostridial neurotoxin of the present invention can be used to augment the endogenous pharmaceutical activity of wild type Clostridial neurotoxins (e.g., BOTOX®), e.g., as a combination therapy.

Derivatives of a Clostridial neurotoxin can be administered as a conjugate with a pharmaceutically acceptable water-soluble polymer moiety. By way of example, a polyethylene glycol conjugate is useful to increase the circulating half-life of the treatment compound, and to reduce the immunogenicity of the molecule. Specific PEG conjugates are described in U.S. Patent Application Publ. No. 2006/0074200 to Daugs et al., which is hereby incorporated by reference in its entirety. Other conjugates include HA, which are described in U.S. Pat. No. 7,879,341 to Taylor and U.S. Patent Application Publication No. 2012/0141532 to Blanda et al., each of which is hereby incorporated by reference in its entirety. Liquid forms, including liposome-encapsulated formulations, are illustrated by injectable solutions and suspensions. Exemplary solid forms include capsules, tablets, and controlled-release forms, such as a miniosmotic pump or an implant. Other dosage forms can be devised by those skilled in the art, as shown, for example, by Ansel and Popovich, Pharmaceutical Dosage Forms and Drug Delivery Systems, 5$^{th}$ Edition (Lea & Febiger 1990), Gennaro (ed.), Remington's Pharmaceutical Sciences, 19$^{th}$ Edition (Mack Publishing Company 1995), and by Ranade and Hollinger, Drug Delivery Systems (CRC Press 1996), each of which is hereby incorporated by reference in its entirety.

According to one embodiment, by treatment it is meant dermatologic or aesthetic treatment (see e.g., Carruthers et al., "Botulinum Toxin A in the Mid and Lower Face and Neck," *Dermatol. Clin.* 22:151-158 (2004); Lang, "History and Uses of BOTOX BOTOX® (Botulinum Toxin Type A)," *Lippincotts Case Manag.* 9:109-112 (2004); Naumann et al., "Safety of Botulinum Toxin Type A: A Systematic Review and Meta-Analysis," *Curr. Med. Res. Opin.* 20:981-990 (2004); Vartanian et al., "Facial Rejuvenation Using Botulinum Toxin A: Review and Updates," *Facial Plast. Surg.* 20:11-19 (2004), which are hereby incorporated by reference in their entirety) as well as therapeutic treatment (see e.g., Bentsianov et al., "Noncosmetic Uses of Botulinum Toxin," *Clin. Dermatol.* 22:82-88 (2004); Carruthers et al., "Botox [BOTOX®]: Beyond Wrinkles," *Clin. Dermatol.* 22:89-93 (2004); Jankovic, "Botulinum Toxin In Clinical Practice," *J. Neurol. Neurosurg. Psychiatry* 75:951-957 (2004); Klein, "The Therapeutic Potential of Botulinum Toxin," *Dermatol. Surg.* 30:452-455 (2004); Schurch, "The Role of Botulinum Toxin in Neurology," *Drugs Today (Banc)* 40:205-212 (2004), which are hereby incorporated by reference in their entirety).

Subjects to be treated pursuant to the method of the present invention include, without limitation, human and non-human primates, or other animals such as dog, cat, horse, cow, goat, sheep, rabbit, or rodent (e.g., mouse or rat).

Preferred treatment methods of the present invention include, but are not limited to, dermatologic or aesthetic treatment, gastroenterologic treatment, genitourinaric treatment, neurologic treatment, oncological treatment, and/or the treatment of any condition characterized by synaptopathology (see, e.g., Brose et al., "Synaptopathies: Dysfunction of Synaptic Function," *Biochem. Soc. Trans.* 38:443-444 (2010); Yu & Lu, "Synapses and Dendritic Spines as Pathogenic Targets in Alzheimer's Disease," *Neural Plasticity* 2012:1-8 (2012); Siskova et al., "Reactive Hypertrophy of Synaptic Varicosities Within the Hippocampus of Prion-Infected Mice," *Biochem Soc. Trans.* 38:471-475 (2010); Warner et al., "TorsinA and DYT1 Dystonia: A Synaptopathy?" *Biochem. Soc. Trans.* 38:452-456 (2010); Rozas et al., "Presynaptic Dysfunction in Huntington's Disease," *Biochem Soc. Trans.* 38:488-492 (2010); and Jones, "Errant Ensembles: Dysfunctional Neuronal Network Dynamics in Schizophrenia," *Biochem. Soc. Trans.* 38:516-521 (2010), which are hereby incorporated by reference in their entirety). Treatment of a condition characterized by synaptopathology may involve the neuromodulation of the synapse by the neurotoxin derivative.

Dermatologic or aesthetic treatment includes, but is not limited to, treatment for Rhtyiddess (wrinkles) (Sadick et al., "Comparison of Botulinum Toxins A and B in the Treatment of Facial Rhytides," *Dermatol. Clin.* 22:221-226 (2004), which is hereby incorporated by reference in its entirety), including glabellar (Carruthers et al., "Botulinum Toxin type A for the Treatment of Glabellar Rhytides," *Dermatol. Clin.* 22:137-144 (2004); Ozsoy et al., "Two-Plane Injection of Botulinum Exotoxin A in Glabellar Frown Lines," *Aesthetic Plast. Surg.* 28:114-115 (2004); which are hereby incorporated by reference in their entirety), neck lines (Brandt et al., "Botulinum Toxin for the Treatment of Neck Lines and Neck Bands," *Dermatol. Clin.* 22:159-166 (2004), which is hereby incorporated by reference in its entirety), crow's feet (Levy et al., "Botulinum Toxin A: A 9-Month Clinical and 3D In Vivo Profilometric Crow's Feet Wrinkle Formation Study," *J. Cosmet. Laser Ther.* 6:16-20 (2004), which is hereby incorporated by reference in its entirety), and brow contour (Chen et al., "Altering Brow Contour with Botulinum Toxin," *Facial Plast. Surg. Clin. North Am.* 11:457-464 (2003), which is hereby incorporated by reference in its entirety). Other dermatologic treatment includes treatment for hypertrophic masseter muscles (Ahn et al., "Botulinum Toxin for Masseter Reduction in Asian Patients," *Arch. Facial Plast. Surg.* 6:188-191 (2004), which is hereby incorporated by reference in its entirety) and focal hyperhydrosis (Glogau, "Treatment of Hyperhidrosis with Botulinum Toxin," *Dermatol. Clin.* 22:177-185, vii (2004), which is hereby incorporated by reference in its entirety), including axillary ("Botulinum Toxin (Botox [BOTOX®]) for Axillary Hyperhidrosis," *Med. Lett. Drugs Ther.* 46:76 (2004), which is hereby incorporated by reference in its entirety) and genital (Lee et al., "A Case of Foul Genital Odor Treated with Botulinum Toxin A," *Dermatol. Surg.* 30:1233-1235 (2004), which is hereby incorporated by reference in its entirety).

Gastroentologic treatment includes, but is not limited to, treatment for esophageal motility disorders (Achem, "Treatment of Spastic Esophageal Motility Disorders," *Gastroenterol. Clin. North Am.* 33:107-124 (2004), which is hereby incorporated by reference in its entirety), pharyngeal-esophageal spasm (Bayles et al., "Operative Prevention and Management of Voice-Limiting Pharyngoesophageal Spasm," *Otolaryngol. Clin. North Am.* 37:547-558 (2004); Chao et al., "Management of Pharyngoesophageal Spasm with Botox [BOTOX®]," *Otolaryngol. Clin. North Am.* 37:559-566 (2004), which are hereby incorporated by reference in their entirety), and anal fissure (Brisinda et al., "Botulinum Neurotoxin to Treat Chronic Anal Fissure: Results of a Randomized 'Botox [BOTOX®] vs. Dysport [DYSPORT®]' Controlled Trial," *Ailment Pharmacol. Ther.* 19:695-701 (2004); Jost et al., "Botulinum Toxin A in Anal Fissure: Why Does it Work?" *Dis. Colon Rectum* 47:257-258 (2004), which are hereby incorporated by reference in their entirety).

Gastroentologic treatment includes, but is not limited to, treatment for esophageal motility disorders (Achem, "Treatment of Spastic Esophageal Motility Disorders," *Gastroenterol. Clin. North Am.* 33:107-124 (2004), which is hereby incorporated by reference in its entirety), pharyngeal-esophageal spasm (Bayles et al., "Operative Prevention and Management of Voice-Limiting Pharyngoesophageal Spasm," *Otolaryngol. Clin. North Am.* 37:547-558 (2004); Chao et al., "Management of Pharyngoesophageal Spasm with Botox," *Otolaryngol. Clin. North Am.* 37:559-566 (2004), which are hereby incorporated by reference in their entirety), and anal fissure (Brisinda et al., "*Botulinum* Neurotoxin to Treat Chronic Anal Fissure: Results of a Randomized 'Botox vs. Dysport' Controlled Trial," *Ailment Pharmacol. Ther.* 19:695-701 (2004); Jost et al., "*Botulinum* Toxin A in Anal Fissure: Why Does it Work?" *Dis. Colon Rectum* 47:257-258 (2004), which are hereby incorporated by reference in their entirety).

Genitourinaric treatment includes, but is not limited to, treatment for neurogenic dysfunction of the urinary tract ("Botulinic Toxin in Patients with Neurogenic Dysfunction of the Lower Urinary Tracts," *Urologia* July-August: 44-48 (2004); Giannantoni et al., "Intravesical Resiniferatoxin Versus *Botulinum*-A Toxin Injections for Neurogenic Detrusor Overactivity: A Prospective Randomized Study," *J. Urol.* 172:240-243 (2004); Reitz et al., "Intravesical Therapy Options for Neurogenic Detrusor Overactivity," *Spinal Cord* 42:267-272 (2004), which are hereby incorporated by reference in their entirety), overactive bladder (Cruz, "Mechanisms Involved in New Therapies for Overactive Bladder," *Urology* 63:65-73 (2004), which is hereby incorporated by reference in its entirety), and neuromodulation of urinary urge incontinence (Abrams, "The Role of Neuromodulation in the Management of Urinary Urge Incontinence," *BJU Int.* 93:1116 (2004), which is hereby incorporated by reference in its entirety).

Neurologic treatment includes, but is not limited to, treatment for tourettes syndrome (Porta et al., "Treatment of Phonic Tics in Patients with Tourette's Syndrome Using *Botulinum* Toxin Type A," *Neurol. Sci.* 24:420-423 (2004), which is hereby incorporated by reference in its entirety) and focal muscle spasticity or dystonias (MacKinnon et al., "Corticospinal Excitability Accompanying Ballistic Wrist Movements in Primary Dystonia," *Mov. Disord.* 19:273-284 (2004), which is hereby incorporated by reference in its entirety), including, but not limited to, treatment for cervical dystonia (Haussermann et al., "Long-Term Follow-Up of Cervical Dystonia Patients Treated with *Botulinum* Toxin A," *Mov. Disord.* 19:303-308 (2004), which is hereby incorporated by reference in its entirety), primary blepharospasm (Defazio et al., "Primary Blepharospasm: Diagnosis and Management," *Drugs* 64:237-244 (2004), which is hereby incorporated by reference in its entirety), hemifacial spasm, post-stroke (Bakheit, "Optimising the Methods of Evaluation of the Effectiveness of *Botulinum* Toxin Treatment of Post-Stroke Muscle Spasticity," *J. Neurol. Neurosurg. Psychiatry* 75:665-666 (2004), which is hereby incorporated by reference in its entirety), spasmodic dysphonia (Bender et al., "Speech Intelligibility in Severe Adductor Spasmodic Dysphonia," *J. Speech Lang. Hear Res.* 47:21-32 (2004), which is hereby incorporated by reference in its entirety), facial nerve disorders (Finn, "*Botulinum* Toxin Type A: Fine-Tuning Treatment of Facial Nerve Injury," *J. Drugs Dermatol.* 3:133-137 (2004), which is hereby incorporated by reference in its entirety), and Rasmussen syndrome (Lozsadi et al., "*Botulinum* Toxin A Improves Involuntary Limb Movements in Rasmussen Syndrome," *Neurology* 62:1233-1234 (2004), which is hereby incorporated by reference in its entirety). Other neurologic treatments include treatment for amputation pain (Kern et al., "Effects of *Botulinum* Toxin Type B on Stump Pain and Involuntary Movements of the Stump," *Am. J. Phys. Med. Rehabil.* 83:396-399 (2004), which is hereby incorporated by reference in its entirety), voice tremor (Adler et al., "*Botulinum* Toxin Type A for Treating Voice Tremor," *Arch. Neurol.* 61:1416-1420 (2004), which is hereby incorporated by reference in its entirety), crocodile tear syndrome (Kyrmizakis et al., "The Use of *Botulinum* Toxin Type A in the Treatment of Frey and Crocodile Tears Syndrome," *J. Oral Maxillofac. Surg.* 62:840-844 (2004), which is hereby incorporated by reference in its entirety), marginal mandibular nerve paralysis, pain control, and anti-nociceptive effects (Cui et al., "Subcutaneous Administration of *Botulinum* Toxin A Reduces Formalin-Induced Pain," *Pain* 107:125-133 (2004) and U.S. Patent Application Publication No. 2012/0064059 to Foster et al., which are hereby incorporated by reference in its entirety), including but not limited to pain after mastectomy (Layeeque et al., "*Botulinum* Toxin Infiltration for Pain Control After Mastectomy and Expander Reconstruction," *Ann. Surg.* 240:608-613 (2004), which is hereby incorporated by reference in its entirety) and chest pain of esophageal origin (Schumulson et al., "Current and Future Treatment of Chest Pain of Presumed Esophageal Origin," *Gastroenterol. Clin. North Am.* 33:93-105 (2004), which is hereby incorporated by reference in its entirety). Another neurologic treatment amenable to the methods of the present invention is headache (Blumenfeld et al., "*Botulinum* Neurotoxin for the Treatment of Migraine and Other Primary Headache Disorders," *Dermatol. Clin.* 22:167-175 (2004), which is hereby incorporated by reference in its entirety).

The method of the present invention is also suitable for treatment of cerebral palsy (Balkrishnan et al., "Longitudinal Examination of Health Outcomes Associated with *Botulinum* Toxin Use in Children with Cerebral Palsy," *J. Surg. Orthop. Adv.* 13:76-80 (2004); Berweck et al., "Use of *Botulinum* Toxin in Pediatric Spasticity (Cerebral Palsy)," *Mov. Disord.* 19:S162-S167 (2004); Pidcock, "The Emerging Role of Therapeutic *Botulinum* Toxin in the Treatment of Cerebral Palsy," *J. Pediatr.* 145:S33-S35 (2004), which are hereby incorporated by reference in their entirety), hip adductor muscle dysfunction in multiple sclerosis (Wissel et al., "*Botulinum* Toxin Treatment of Hip Adductor Spasticity in Multiple Sclerosis," *Wien Klin Wochesnchr* 4:20-24 (2001), which is hereby incorporated by reference in its entirety), neurogenic pain and inflammation, including arthritis, iatrogenic parotid sialocele (Capaccio et al., "Diagnosis and Therapeutic Management of Iatrogenic Parotid Sialocele," *Ann. Otol. Rhinol. Laryngol.* 113:562-564 (2004), which is hereby incorporated by reference in its entirety), and chronic TMJ pain and displacement (Aquilina et al., "Reduction of a Chronic Bilateral Temporomandibular Joint Dislocation with Intermaxillary Fixation and *Botulinum* Toxin A," *Br. J. Oral Maxillofac. Surg.* 42:272-273 (2004), which is hereby incorporated by reference in its entirety). Other conditions that can be treated by local controlled delivery of pharmaceutically active neurotoxin derivatives include intra-articular administration for the treatment of arthritic conditions (Mahowald et al., "Long Term Effects of Intra-Articular BoNT A for Refractory Joint Pain," *Annual Meeting of the American College of Rheumatology* (2004), which is hereby incorporated by reference in its entirety), and local administration for the treatment of joint contracture (Russman et al., "Cerebral Palsy: A Rational Approach to a Treatment Protocol, and the Role of *Botulinum* Toxin in Treatment," *Muscle Nerve Suppl.* 6:S181-S193 (1997); Pucinelli et al., "Botulinic Toxin for the Rehabilitation of Osteoarthritis Fixed-Flexion Knee Deformity," *Annual Meeting of the Osteoarthitis Research Society International* (2004), which are hereby incorporated by reference in their entirety). The methods of the present invention are also suitable for the treatment of pain associated with various conditions characterized by the sensitization of nociceptors and their associated clinical syndromes, as described in Bach-Rojecky et al., "Antinociceptive Effect of *Botulinum* Toxin Type A In Rat Model of Carrageenan and Capsaicin Induced Pain," *Croat. Med. J.* 46:201-208 (2005); Aoki, "Evidence for Antinociceptive Activity of *Botulinum* Toxin Type A in Pain Management," *Headache* 43 Suppl 1:S9-15 (2003); Kramer et al., "*Botulinum* Toxin A Reduces Neurogenic Flare But Has Almost No Effect on Pain and Hyperalgesia in Human Skin," *J. Neurol.* 250:188-193 (2003); Blersch et al., "*Botulinum* Toxin A and the Cutaneous Nociception in Humans: A Prospective, Double-Blind, Placebo-Controlled, Randomized Study," *J. Neurol. Sci.* 205:59-63 (2002), which are hereby incorporated by reference in its entirety.

The neurotoxin derivatives may be customized to optimize therapeutic properties (See e.g., Chaddock et al., "Retargeted Clostridial Endopeptidases: Inhibition of Nociceptive Neurotransmitter Release In Vitro, and Antinociceptive Activity in In Vivo Models of Pain," *Mov. Disord.* 8:S42-S47 (2004); Finn, "*Botulinum* Toxin Type A: Fine-Tuning Treatment of Facial Nerve Injury," *J. Drugs Dermatol.* 3:133-137 (2004); Eleopra et al., "Different Types of *Botulinum* Toxin in Humans," *Mov. Disord.* 8:S53-S59 (2004); Flynn, "Myobloc," *Dermatol. Clin.* 22:207-211 (2004); and Sampaio et al., "Clinical Comparability of Marketed Formulations of *Botulinum* Toxin," *Mov. Disord.* 8:S129-S136 (2004), which are hereby incorporated by reference in their entirety).

The derivative of a Clostridial neurotoxin may also be used, pursuant to the treatment method of the present invention, to treat diseases influenced by activity-dependent changes in synaptic structure (e.g., synaptopathologies) or hyperactivity of synapse forming apparatus (e.g., tubulin polymerization), and conditions associated with the proliferation of microtubules. For example, Alzheimer's Disease, Parkinson's Disease, and neuronal cancers (of both neural and glial origin). Other conditions that may be treated by the method of the present invention include conditions where the synaptic complex is a disease target.

In one embodiment, neurotoxin derivatives of the present invention accumulate within neuronal cytosol in higher amounts than wild-type Clostridial neurotoxin.

EXAMPLES

Example 1

In-vivo Pharmaceutical Activity Experiments for BoNT A/ad-0

Material and Methods

An atoxic derivative of *Clostridium botulinum* serotype A ("BoNT A/ad"), as described in U.S. Pat. No. 7,785,606 to Ichtchenko and Band (which is hereby incorporated by reference in its entirety), was expressed as described. Since this neurotoxin derivative is atoxic and does not possess a cargo attachment peptide sequence at its N-terminus, it was designated "BoNT A/ad-0," where "ad-0" means atoxic derivative with no cargo site (0), as described herein. BoNT A/ad-0 was purified to electrophoretic homogeneity and activated by specific protease cleavage as described in Band et al., "Recombinant Derivatives of *Botulinum* Neurotoxin A Engineered for Trafficking Studies and Neuronal Delivery," *Protein Expression & Purification* 71:62 (2010), which is hereby incorporated by reference in its entirety. The purified protein was prepared as a stock at a concentration of 10 mg/ml in PBS containing 40% glycerol for stabilization. The studies described below, evaluate the recombinant molecule's toxicity and pharmacologic activity.

Animals

Mice: female Balb/C mice, 5 to 7 weeks old; weight around 19+/−3 grams.

Digit Abduction Score (DAS) Assay

A modification of the classic mouse Digit Abduction Scoring ("DAS") assay was used to determine local pharmacologic activity in muscle, measured by muscle weakening effectiveness, as described in Aoki, "Preclinical Update on BOTOX® (*Botulinum* Toxin Type A)-Purified Neurotoxin Complex Relative to Other *Botulinum* Neurotoxin Preparations," *European Journal of Neurology* (1999), which is hereby incorporated by reference in its entirety. In the DAS Assay, mice are suspended by their tails briefly to elicit a characteristic startle response in which the animal extends its hind limbs and abducts its hind digits. The DAS assay is especially useful to compare the muscle weakening effectiveness of different BoNT preparations (Aoki, "Preclinical Update on BOTOX® (*Botulinum* Toxin Type A)-Purified Neurotoxin Complex Relative to Other *Botulinum* Neurotoxin Preparations," *European Journal of Neurology* (1999) and Aoki, "A Comparison of the Safety Margins of *Botulinum* Neurotoxin Serotypes A, B, and F In Mice," *Toxicon* 39:1815-1820 (2001), which are hereby incorporated by reference in their entirety).

This test was utilized to define pharmacological activity of BoNT A/ad-0 in mice. Mice were scored as having a positive DAS response when they were unable to fully extend all digits on the injected leg. A negative score is given to mice that spread the toes of the injected leg comparable to that of the non-injected leg.

Female Balb/C mice were given unilateral gastrocnemius intramuscular injections with the concentration described in a volume of 3 µl of 0.9% NaCl using a 25 µl Hamilton syringe. Muscle weakness was assessed from day 1 until 5 days post injection by suspending the mice in order to elicit a characteristic startle response and observing whether the toes on the injected leg were spreading compared to the non injected leg.

Measuring Paralysis

Definitive paralysis is described using two independent variables. First, the inability to use the injected leg to walk (paralysis); and second, the inability to spread the toes on the injected leg (digital abduction).

Results: Toxicity, $LD_{50}$

The BoNT A/ad-0 preparation described above was used for the following toxicity study. The study was designed to approximate the standard murine $LD_{50}$ test for wild type BoNT A ("wt BoNT A").

A total of 30 female mice were used in this study. Each mouse was injected intraperitoneally with the indicated dose of BoNT A/ad-0 in 200 µl of PBS (Table 1), and observed for 24 hours.

Doses ranging from 0.5 µg/mouse to 2 µg/mouse, based on the $LD_{50}$ published by Pellett et al., "Neuronal Targeting, Internalization, and Biological Activity of a Recombinant Atoxic Derivative of *Botulinum* Neurotoxin A," *Biochemical & Biophysical Research Communications* 405(4):673-677 (2011), which is hereby incorporated by reference in its entirety), using BoNT A/ad (1.2 µg per mouse or 50 µg/kg body weight. The $LD_{50}$ for BoNT A/ad-0 was found to be very similar to that for BoNT A/ad (Table 1). Briefly, 50% or 5 out of 10 mice injected with a dose of 50 µg/kg body weight showed symptoms of botulism intoxication by 36 hours. All mice injected with a dose of 2 µg, which is approximately 83.3 µg/kg body weight, expired within 48 hours. From this study it is concluded that 50 µg/kg body weight is the approximate $LD_{50}$ of BoNT A/ad-0.

TABLE 1

Results of Toxicity (LD50) Study for BoNT A/ad-0

| Injected Dose | No. Mice | Dead | Survive |
|---|---|---|---|
| 2 µg | 10 | 10 | 0 |
| 1.2 µg | 10 | 5 | 5 |
| 1 µg | 5 | 1 | 4 |
| 0.5 µg | 5 | 0 | 5 |

The $LD_{50}$ of wt BoNT A is approximately 0.5 ng/kg (Aoki, "A Comparison of the Safety Margins of Botulinum Neurotoxin Serotypes A, B, and F In Mice," *Toxicon* 39:1815-1820 (2001), which is hereby incorporated by reference in its entirety), or 100,000-fold lower than that of BoNT A/ad-0. Because of this toxicity, the effectiveness of wt BoNT A at extremely low doses, and the variability in potency for BoNTs produced from a wild type bacterial source, pharmacological doses of wt BoNT A are generally specified in terms of "activity units," with 1 mouse $LD_{50}$ of wt BoNT A considered to be 1 activity unit, or approximately 0.5 ng/kg of wt BoNT A (Aoki, "A Comparison of the Safety Margins of Botulinum Neurotoxin Serotypes A, B, and F In Mice," *Toxicon* 39:1815-1820 (2001), which is hereby incorporated by reference in its entirety). This takes into account concentration variations in the level of active toxin between preparations and manufacturers. Harmonized standards across producers remain undefined. This is due to both different manufacturing methods and batch-to-batch variation, but is also related to marketing claims. The final pharmaceutical preparations are formulated with albumin (BOTOX®) and/or lactose (DYSPORT®). From the $LD_{50}$ results described here, it can be concluded that 1 $LD_{50}$ Unit (1U) of BoNT A/ad-0 corresponds to a dose of approximately 50 µg/kg, or approximately 1.2 µg per mouse.

Results: Muscle Paralysis Study/DAS Assay for Pharmacologic Activity In Vivo

BoNT A/ad-0 described above was tested in the murine DAS to determine if BoNT A/ad-0 possesses pharmacological activity at doses significantly below its $LD_{50}$, and whether it displays typical dose-response activity. Mice were injected in the gastrocnemius muscle with 3 µl of BoNT A/ad-0 in 0.9% NaCl using a 25 µl Hamilton Syringe. The doses administered are expressed as the µg administered per mouse, or units of BoNT A/ad-0 activity administered per mouse (Table 2).

Two observations are noted to categorize a mouse as positive for muscle paralysis induced by administration of BoNT A/ad-0. First, by the inability of the mouse to use the injected leg to walk (muscle paralysis). Second, by observing whether the digits on the injected leg appeared collapsed (digital abduction). Definite muscle paralysis was initially observed and recorded 24 hours after the initial administration. Mice were daily evaluated for definitive muscle paralysis for a maximum of 5 days.

The results of this pharmacologic study of BoNT A/ad-0 are shown in Table 2 and FIG. 2. Mice administered doses ranging from 0.008 $LD_{50}$ units (0.01 µg) to 0.42 $LD_{50}$ units (0.5 µg) of BoNT A/ad-0 showed definitive muscle paralysis and digital abduction (FIG. 2 and Table 2), without any signs of mortality. In fact, 4 out of 5 animals injected with 0.01 µg presented with muscle paralysis and some degree of digital abduction (Table 2), indicating that the $ED_{50}$ for BoNT A/ad-0, the lowest dose at which 50% of the injected animals demonstrate the intended pharmacologic activity, is 0.01 µg or lower, which corresponds to 0.008 $LD_{50}$ units or lower. All mice that presented paralysis on day 1 continued to present paralysis to the end of the study, day 5. No signs of systemic toxicity were observed in any of the mice in this study.

These data confirm that BoNT A/ad-0 has similar pharmaceutical properties compared to wt BoNT A, albeit with a dose-response profile, a significantly increased range of safe therapeutic activity and, therefore, an improved therapeutic index, and an improved safety margin. This comparison of BoNT A/ad-0 to pharmaceutical preparations of wt BoNT is illustrated in Table 3, and contrasted to the data reported by Aoki, "A Comparison of the Safety Margins of Botulinum Neurotoxin Serotypes A, B, and F In Mice," *Toxicon* 39:1815-1820 (2001), which is hereby incorporated by reference in its entirety. For instance, Aoki, "A Comparison of the Safety Margins of Botulinum Neurotoxin Serotypes A, B, and F In Mice," *Toxicon* 39:1815-1820 (2001), which is hereby incorporated by reference in its entirety, reported that the safety margin for BOTOX® is about 13.9+/−1.7 and for DYSPORT® 7.6+/−0.9. Here it is shown that at the lowest dose of BoNT A/ad-0 studied, 0.01 µg, definite paralysisis was observed in 4/5 mice. This dose can be considered a conservative estimate of the $ED_{50}$. Therefore, for BoNT A/ad-0, the safety margin is approximately 120, or expressed differently, approximately 10-fold better than that for BOTOX® or DYSPORT® (Table 3).

TABLE 2

Results of Pharmacologic Study of BoNT A/ad-0

| Dose Injected per Mouse | $LD_{50}$ Units | No. Mice | No. with Definitive Paralysis | No. Dead |
|---|---|---|---|---|
| 0 (placebo) | 0 | 9 | 0 | 0 |
| 0.01 µg | 0.008 | 5 | 4 | 0 |
| 0.1 µg | 0.08 | 5 | 5 | 0 |
| 0.5 µg | 0.42 | 10 | 10 | 0 |
| 1 µg | 0.83 | 5 | 5 | 0 |
| 1.2 µg | 1 | 5 | 2 | 3 |
| 1.5 µg | 1.25 | 5 | 1 | 4 |

Naïve mice were administered BoNT A/ad-0 in the left gastrocnemius via intramuscular injection with 3 µl containing the indicated mass or units of BoNT A/ad-0.

TABLE 3

LD50 and ED50 of BoNT A/ad-0

$LD_{50}$ = ~1.2 µg
$ED_{50}$ = ~0.01 ug ($ED_{50}$ = 0.01 µg or lower)
$LD_{50}/ED_{50}$ = safety margin = ~120

If expressed as units, the $ED_{50}$ of BoNT A/ad-0 is 0.008 $LD_{50}$ units, or lower.

Comparison to Prior Studies and Conclusions

Prior studies have found that mutations introduced into the light chain of recombinant BoNT A/ad (a molecule containing a cargo attachment peptide as described in U.S. Patent Application Publication No. 2011/0206616 to Ichtchenko and Band, which is hereby incorporated by reference in its entirety) increased the $LD_{50}$ of the toxin by 100,000-fold. In particular, injections of 0.5 µg (n=25) or 1 µg (n=15) of BoNT A/ad (in the absence of any therapeutic agent) were made into the tibialis muscle two months prior to administration of the repeat dose to each animal. The repeat dose, consisting of 3 µl containing the indicated quantitites of BoNT A/ad, 1 µg (n=18) or 2 µg (n=20), were similarly injected into the tibialis muscle. These data (Table 4 and Table 5) suggest that immune resistance to BoNT A/ad is not developing with repeat treatment.

TABLE 4

BoNT A/ad Induces Paralysis

| Dose | No. Mice | No. with Definitive Paralysis | No. Dead (within 48 hrs) |
|---|---|---|---|
| 0 (placebo) | 21 | 0 | 0 |
| 0.5 µg | 38 | 34 | 0 |
| 1 µg | 15 | 12 | 1 |
| 1.2 µg | 10 | 5 | 5 |

1.2 µg is the apparent $LD_{50}$ for intramuscular injections of BoNT A/ad estimated from this experiment.

TABLE 5

Paralytic Effect After Re-injection of BoNT A/ad

| Repeat Dose | No. Mice | No. with Definitive Paralysis | No. Dead (within 48 hrs) |
|---|---|---|---|
| 1 µg | 18 | 17 | 0 |
| 2 µg | 20 | | 15 dead, with 3 appearing sick. 2 mice appeared normal at 48 hrs. |

In the present study it was found that the $LD_{50}$ of BoNT A/ad-0, which has identical toxin-disabling mutations as BoNT A/ad, is likewise elevated ~100,000-fold relative to wt BoNT A. But surprisingly, it was observed that BoNT A/ad-0 still possessed pharmacologic activity similar to that observed for wt BoNT A, and that a therapeutic agent need not be delivered via the cargo site of BoNT/A ad to render it therapeutic. By comparing the dose-response of BoNT A/ad-0 to that reported for pharmaceutical preparations of wt BoNT A, it can be concluded that BoNT A/ad-0 can be used for pharmaceutical treatments in the same way as wt BoNTs, but with significantly reduced danger of systemic toxicity, and thus significant improved safety advantages for clinical use.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A treatment method comprising:
    selecting a subject in need of therapeutic treatment involving induction of muscle paralysis and
    contacting the subject with an isolated, physiologically active derivative of a wild type *Clostridium botulinum* neurotoxin, wherein the derivative of a *Clostridium botulinum* neurotoxin comprises one or more amino acid substitutions relative to the wild type *Clostridium botulinum* neurotoxin that reduces the metalloprotease activity responsible for the toxicity of wild type *Clostridium botulinum* neurotoxin and wherein the neurotoxin derivative comprises:
    a light chain region and
    a heavy chain region, wherein the light and heavy chain regions are linked by a disulfide bond, and wherein the light and heavy chain regions are not truncated,
    said contacting being carried out to induce muscle paralysis in the subject to treat the subject, with the proviso that the neurotoxin derivative does not possess a cargo attachment peptide sequence at its N-terminus.

2. The method according to claim 1, wherein the derivative of a *Clostridium botulinum* neurotoxin is a derivative of *Clostridium botulinum* serotype A, *Clostridium botulinum* serotype B, *Clostridium botulinum* serotype C, *Clostridium botulinum* serotype D, *Clostridium botulinum* serotype E, *Clostridium botulinum* serotype F, or *Clostridium botulinum* serotype G.

3. The method according to claim 1, wherein the derivative of a *Clostridium botulinum* neurotoxin is a recombinant protein.

4. The method according to claim 1, wherein the treatment is for a dermatologic or aesthetic condition selected from the group consisting of Rhytides, hypertrophic masseter muscles, and focal hyperhydrosis.

5. The method according to claim 1, wherein the treatment is for a gastroenterological condition selected from the group consisting of esophageal motility disorders, pharyngeal-esophageal spasm, and anal fissure.

6. The method according to claim 1, wherein the treatment is for a genitourinaric condition selected from the group consisting of neurogenic dysfunction of the urinary tract, overactive bladder, and neuromodulation of urinary urge incontinence.

7. The method according to claim 1, wherein the treatment is for a neurologic condition selected from the group consisting of tourettes syndrome, focal muscle spasticity or dystonias, cervical dystonia, primary blepharospasm, hemifacial spasm, spasmodic dysphonia, facial nerve disorders, Rasmussen syndrome, amputation pain, voice tremor, crocodile tear syndrome, marginal mandibular nerve paralysis, pain, chest pain of esophageal origin, headache, cerebral palsy, hip adductor muscle dysfunction in multiple sclerosis, neurogenic pain and inflammation, arthritis, iatrogenic parotid sialocele, and chronic TMJ pain and displacement.

8. The method according to claim 1, wherein the derivative of a *Clostridium botulinum* neurotoxin has an $LD_{50}$ that is at least 1,000-fold higher than the $LD_{50}$ of the corresponding wild-type *Clostridium botulinum* neurotoxin.

9. The method according to claim 1, wherein the derivative of a *Clostridium botulinum* neurotoxin accumulates within neuronal cytosol in higher amounts than the corresponding wild-type *Clostridium botulinum* neurotoxin.

10. The method according to claim 1, wherein the derivative of a wild type *Clostridium botulinum* neurotoxin is produced by cleaving a propeptide, wherein the propeptide comprises:
    a light chain region;
    a heavy chain region; and
    an intermediate region connecting the light and heavy chain regions and comprising a highly specific protease cleavage site, wherein said highly specific protease cleavage site has three or more specific adjacent amino acid residues that are recognized by the highly specific protease in order to enable cleavage.

11. The method according to claim 10, wherein the highly specific protease cleavage site is selected from an enterokinase cleavage site and a tobacco etch virus protease recognition (TEV) sequence.

12. The method according to claim 10, wherein the propeptide has no low-specificity protease cleavage sites in the intermediate region, said low-specificity protease cleavage sites having two or less adjacent amino acid residues that are recognized by a protease in order to permit cleavage.

13. The method according to claim 10, wherein the propeptide further comprises a signal peptide coupled to the light chain region, wherein the signal peptide is suitable to permit secretion of the neurotoxin propeptide from a eukaryotic cell to a medium.

14. The method according to claim 13, wherein the signal peptide is a gp64 signal peptide.

15. The method according to claim 13, wherein the propeptide further comprises an affinity tag located between the signal peptide and the light chain region.

16. The method according to claim 15, wherein the affinity tag has a sequence of SEQ ID NO:10.

17. The method according to claim 1, wherein the heavy chain has no trypsin-susceptible recognition sequences.

18. The method according to claim 1, wherein the wild type *Clostridium botulinum* neurotoxin is selected from SEQ ID NO:1, SEQ ID NO:2, SEQ ID NO:3, SEQ ID NO:4, SEQ ID NO:5, SEQ ID NO:6, or SEQ ID NO: 7.

19. The method according to claim 1, wherein the derivative of a *Clostridium botulinum* neurotoxin is selected from SEQ ID NO:1, SEQ ID NO:2, SEQ ID NO:3, SEQ ID NO:4, SEQ ID NO:5, SEQ ID NO:6, or SEQ ID NO:7 comprising an amino acid substitution in the light chain region.

20. The method according to claim 19, wherein the amino acid substitution is in a metalloprotease site.

21. The method according to claim 1, wherein the derivative of a *Clostridium botulinum* neurotoxin is selected from SEQ ID NO:1, SEQ ID NO: 2, SEQ ID NO:3, SEQ ID NO:4, SEQ ID NO:5, SEQ ID NO:6, or SEQ ID NO:7 comprising a non-native motif in the light chain region.

* * * * *

SEQUENCE LISTING

<160> NUMBER OF SEQ ID NOS: 10

<210> SEQ ID NO 1
<211> LENGTH: 1296
<212> TYPE: PRT
<213> ORGANISM: Clostridium botulinum (serotype A)

<400> SEQUENCE: 1

```
Met Pro Phe Val Asn Lys Gln Phe Asn Tyr Lys Asp Pro Val Asn Gly
  1               5                  10                  15

Val Asp Ile Ala Tyr Ile Lys Ile Pro Asn Ala Gly Gln Met Gln Pro
             20                  25                  30

Val Lys Ala Phe Lys Ile His Asn Lys Ile Trp Val Ile Pro Glu Arg
         35                  40                  45

Asp Thr Phe Thr Asn Pro Glu Glu Gly Asp Leu Asn Pro Pro Pro Glu
     50                  55                  60

Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
    290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Thr Thr Glu Asp
            340                 345                 350

Asn Phe Val Lys Phe Phe Lys Val Leu Asn Arg Lys Thr Tyr Leu Asn
        355                 360                 365
```

```
Phe Asp Lys Ala Val Phe Lys Ile Asn Ile Val Pro Lys Val Asn Tyr
370                 375                 380
Thr Ile Tyr Asp Gly Phe Asn Leu Arg Asn Thr Asn Leu Ala Ala Asn
385                 390                 395                 400
Phe Asn Gly Gln Asn Thr Glu Ile Asn Asn Met Asn Phe Thr Lys Leu
            405                 410                 415
Lys Asn Phe Thr Gly Leu Phe Glu Phe Tyr Lys Leu Leu Cys Val Arg
            420                 425                 430
Gly Ile Ile Thr Ser Lys Thr Lys Ser Leu Asp Lys Gly Tyr Asn Lys
            435                 440                 445
Ala Leu Asn Asp Leu Cys Ile Lys Val Asn Asn Trp Asp Leu Phe Phe
450                 455                 460
Ser Pro Ser Glu Asp Asn Phe Thr Asn Asp Leu Asn Lys Gly Glu Glu
465                 470                 475                 480
Ile Thr Ser Asp Thr Asn Ile Glu Ala Ala Glu Asn Ile Ser Leu
                485                 490                 495
Asp Leu Ile Gln Gln Tyr Tyr Leu Thr Phe Asn Phe Asp Asn Glu Pro
            500                 505                 510
Glu Asn Ile Ser Ile Glu Asn Leu Ser Ser Asp Ile Ile Gly Gln Leu
            515                 520                 525
Glu Leu Met Pro Asn Ile Glu Arg Phe Pro Asn Gly Lys Lys Tyr Glu
530                 535                 540
Leu Asp Lys Tyr Thr Met Phe His Tyr Leu Arg Ala Gln Glu Phe Glu
545                 550                 555                 560
His Gly Lys Ser Arg Ile Ala Leu Thr Asn Ser Val Asn Glu Ala Leu
            565                 570                 575
Leu Asn Pro Ser Arg Val Tyr Thr Phe Phe Ser Ser Asp Tyr Val Lys
            580                 585                 590
Lys Val Asn Lys Ala Thr Glu Ala Ala Met Phe Leu Gly Trp Val Glu
            595                 600                 605
Gln Leu Val Tyr Asp Phe Thr Asp Glu Thr Ser Glu Val Ser Thr Thr
610                 615                 620
Asp Lys Ile Ala Asp Ile Thr Ile Ile Pro Tyr Ile Gly Pro Ala
625                 630                 635                 640
Leu Asn Ile Gly Asn Met Leu Tyr Lys Asp Asp Phe Val Gly Ala Leu
            645                 650                 655
Ile Phe Ser Gly Ala Val Ile Leu Leu Glu Phe Ile Pro Glu Ile Ala
            660                 665                 670
Ile Pro Val Leu Gly Thr Phe Ala Leu Val Ser Tyr Ile Ala Asn Lys
            675                 680                 685
Val Leu Thr Val Gln Thr Ile Asp Asn Ala Leu Ser Lys Arg Asn Glu
            690                 695                 700
Lys Trp Asp Glu Val Tyr Lys Tyr Ile Val Thr Asn Trp Leu Ala Lys
705                 710                 715                 720
Val Asn Thr Gln Ile Asp Leu Ile Arg Lys Lys Met Lys Glu Ala Leu
            725                 730                 735
Glu Asn Gln Ala Glu Ala Thr Lys Ala Ile Ile Asn Tyr Gln Tyr Asn
            740                 745                 750
Gln Tyr Thr Glu Glu Glu Lys Asn Asn Ile Asn Phe Asn Ile Asp Asp
            755                 760                 765
Leu Ser Ser Lys Leu Asn Glu Ser Ile Asn Lys Ala Met Ile Asn Ile
770                 775                 780
```

```
Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
                900                 905                 910

Gln Ile Gln Leu Phe Asn Leu Glu Ser Ser Lys Ile Glu Val Ile Leu
                915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
                980                 985                 990

Ile Lys Gln Arg Val Val Phe Lys Tyr Ser Gln Met Ile Asn Ile Ser
                995                 1000                1005

Asp Tyr Ile Asn Arg Trp Ile Phe Val Thr Ile Thr Asn Asn Arg
    1010                1015                1020

Leu Asn Asn Ser Lys Ile Tyr Ile Asn Gly Arg Leu Ile Asp Gln
    1025                1030                1035

Lys Pro Ile Ser Asn Leu Gly Asn Ile His Ala Ser Asn Asn Ile
    1040                1045                1050

Met Phe Lys Leu Asp Gly Cys Arg Asp Thr His Arg Tyr Ile Trp
    1055                1060                1065

Ile Lys Tyr Phe Asn Leu Phe Asp Lys Glu Leu Asn Glu Lys Glu
    1070                1075                1080

Ile Lys Asp Leu Tyr Asp Asn Gln Ser Asn Ser Gly Ile Leu Lys
    1085                1090                1095

Asp Phe Trp Gly Asp Tyr Leu Gln Tyr Asp Lys Pro Tyr Tyr Met
    1100                1105                1110

Leu Asn Leu Tyr Asp Pro Asn Lys Tyr Val Asp Val Asn Asn Val
    1115                1120                1125

Gly Ile Arg Gly Tyr Met Tyr Leu Lys Gly Pro Arg Gly Ser Val
    1130                1135                1140

Met Thr Thr Asn Ile Tyr Leu Asn Ser Ser Leu Tyr Arg Gly Thr
    1145                1150                1155

Lys Phe Ile Ile Lys Lys Tyr Ala Ser Gly Asn Lys Asp Asn Ile
    1160                1165                1170

Val Arg Asn Asn Asp Arg Val Tyr Ile Asn Val Val Val Lys Asn
    1175                1180                1185
```

-continued

```
Lys Glu Tyr Arg Leu Ala Thr Asn Ala Ser Gln Ala Gly Val Glu
    1190                1195                1200

Lys Ile Leu Ser Ala Leu Glu Ile Pro Asp Val Gly Asn Leu Ser
    1205                1210                1215

Gln Val Val Val Met Lys Ser Lys Asn Asp Gln Gly Ile Thr Asn
    1220                1225                1230

Lys Cys Lys Met Asn Leu Gln Asp Asn Asn Gly Asn Asp Ile Gly
    1235                1240                1245

Phe Ile Gly Phe His Gln Phe Asn Asn Ile Ala Lys Leu Val Ala
    1250                1255                1260

Ser Asn Trp Tyr Asn Arg Gln Ile Glu Arg Ser Ser Arg Thr Leu
    1265                1270                1275

Gly Cys Ser Trp Glu Phe Ile Pro Val Asp Asp Gly Trp Gly Glu
    1280                1285                1290

Arg Pro Leu
    1295

<210> SEQ ID NO 2
<211> LENGTH: 1291
<212> TYPE: PRT
<213> ORGANISM: Clostridium botulinum (serotype B)

<400> SEQUENCE: 2

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255
```

```
Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
        290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
            355                 360                 365

Thr Arg Ala Ser Tyr Phe Ser Asp Ser Leu Pro Pro Val Lys Ile Lys
        370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
            435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
            515                 520                 525

Lys Ile Phe Thr Asp Glu Asn Thr Ile Phe Gln Tyr Leu Tyr Ser Gln
        530                 535                 540

Thr Phe Pro Leu Asp Ile Arg Asp Ile Ser Leu Thr Ser Ser Phe Asp
545                 550                 555                 560

Asp Ala Leu Leu Phe Ser Asn Lys Val Tyr Ser Phe Ser Met Asp
                565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
        610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
            660                 665                 670
```

-continued

```
Asp Asn Lys Asn Lys Ile Ile Lys Thr Ile Asp Asn Ala Leu Thr Lys
        675                 680                 685

Arg Asn Glu Lys Trp Ser Asp Met Tyr Gly Leu Ile Val Ala Gln Trp
    690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Lys Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
        770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
                820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
        850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
        915                 920                 925

Ser Phe Trp Ile Arg Ile Pro Lys Tyr Lys Asn Asp Gly Ile Gln Asn
    930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990

Glu Asp Ile Ser Glu Tyr Ile Asn Arg Trp Phe Phe Val Thr Ile Thr
        995                1000                1005

Asn Asn Leu Asn Asn Ala Lys Ile Tyr Ile Asn Gly Lys Leu Glu
        1010                1015                1020

Ser Asn Thr Asp Ile Lys Asp Ile Arg Glu Val Ile Ala Asn Gly
        1025                1030                1035

Glu Ile Ile Phe Lys Leu Asp Gly Asp Ile Asp Arg Thr Gln Phe
        1040                1045                1050

Ile Trp Met Lys Tyr Phe Ser Ile Phe Asn Thr Glu Leu Ser Gln
        1055                1060                1065

Ser Asn Ile Glu Glu Arg Tyr Lys Ile Gln Ser Tyr Ser Glu Tyr
        1070                1075                1080
```

```
Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Pro Val Gly Glu Ile Leu Thr Arg Ser Lys Tyr Asn
    1115                1120                1125

Gln Asn Ser Lys Tyr Ile Asn Tyr Arg Asp Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Thr Tyr Lys Tyr Phe Lys Lys
    1175                1180                1185

Glu Glu Glu Lys Leu Phe Leu Ala Pro Ile Ser Asp Ser Asp Glu
    1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245

Val Phe Glu Glu Tyr Lys Asp Tyr Phe Cys Ile Ser Lys Trp Tyr
    1250                1255                1260

Leu Lys Glu Val Lys Arg Lys Pro Tyr Asn Leu Lys Leu Gly Cys
    1265                1270                1275

Asn Trp Gln Phe Ile Pro Lys Asp Glu Gly Trp Thr Glu
    1280                1285                1290

<210> SEQ ID NO 3
<211> LENGTH: 1291
<212> TYPE: PRT
<213> ORGANISM: Clostridium botulinum (serotype C)

<400> SEQUENCE: 3

Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Thr Gly Asn Ile Trp Val Ile Pro Asp
        35                  40                  45

Arg Phe Ser Arg Asn Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Asp Lys Asp Pro Phe Leu Lys Glu Ile Ile Lys Leu Phe Lys Arg
                85                  90                  95

Ile Asn Ser Arg Glu Ile Gly Glu Glu Leu Ile Tyr Arg Leu Ser Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160
```

```
Pro Arg Glu Asn Ile Ile Asp Pro Glu Thr Ser Thr Phe Lys Leu Thr
            165                 170                 175

Asn Asn Thr Phe Ala Ala Gln Glu Gly Phe Gly Ala Leu Ser Ile Ile
        180                 185                 190

Ser Ile Ser Pro Arg Phe Met Leu Thr Tyr Ser Asn Ala Thr Asn Asp
    195                 200                 205

Val Gly Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
        260                 265                 270

Phe Gly Gly Pro Thr Ile Asp Leu Ile Pro Lys Ser Ala Arg Lys Tyr
    275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
        340                 345                 350

Glu Leu Thr Gln Ile Phe Thr Glu Phe Asn Tyr Ala Lys Ile Tyr Asn
    355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
        420                 425                 430

Phe Thr Lys Phe Cys His Lys Ala Ile Asp Gly Arg Ser Leu Tyr Asn
    435                 440                 445

Lys Thr Leu Asp Cys Arg Glu Leu Leu Val Lys Asn Thr Asp Leu Pro
450                 455                 460

Phe Ile Gly Asp Ile Ser Asp Val Lys Thr Asp Ile Phe Leu Arg Lys
465                 470                 475                 480

Asp Ile Asn Glu Glu Thr Glu Val Ile Tyr Tyr Pro Asp Asn Val Ser
                485                 490                 495

Val Asp Gln Val Ile Leu Ser Lys Asn Thr Ser Glu His Gly Gln Leu
        500                 505                 510

Asp Leu Leu Tyr Pro Ser Ile Asp Ser Glu Ser Glu Ile Leu Pro Gly
    515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Arg Ser Ile Glu Glu Ala Leu Asp Asn Ser Ala
                565                 570                 575
```

-continued

```
Lys Val Tyr Thr Tyr Phe Pro Thr Leu Ala Asn Lys Val Asn Ala Gly
            580                 585                 590
Val Gln Gly Gly Leu Phe Leu Met Trp Ala Asn Asp Val Val Glu Asp
        595                 600                 605
Phe Thr Thr Asn Ile Leu Arg Lys Asp Thr Leu Asp Lys Ile Ser Asp
        610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
                645                 650                 655
Thr Ile Leu Leu Glu Ala Phe Pro Glu Phe Thr Ile Pro Ala Leu Gly
            660                 665                 670
Ala Phe Val Ile Tyr Ser Lys Val Gln Glu Arg Asn Glu Ile Ile Lys
        675                 680                 685
Thr Ile Asp Asn Cys Leu Glu Gln Arg Ile Lys Arg Trp Lys Asp Ser
        690                 695                 700
Tyr Glu Trp Met Met Gly Thr Trp Leu Ser Arg Ile Ile Thr Gln Phe
705                 710                 715                 720
Asn Asn Ile Ser Tyr Gln Met Tyr Asp Ser Leu Asn Tyr Gln Ala Gly
                725                 730                 735
Ala Ile Lys Ala Lys Ile Asp Leu Glu Tyr Lys Lys Tyr Ser Gly Ser
            740                 745                 750
Asp Lys Glu Asn Ile Lys Ser Gln Val Glu Asn Leu Lys Asn Ser Leu
        755                 760                 765
Asp Val Lys Ile Ser Glu Ala Met Asn Asn Ile Asn Lys Phe Ile Arg
        770                 775                 780
Glu Cys Ser Val Thr Tyr Leu Phe Lys Asn Met Leu Pro Lys Val Ile
785                 790                 795                 800
Asp Glu Leu Asn Glu Phe Asp Arg Asn Thr Lys Ala Lys Leu Ile Asn
                805                 810                 815
Leu Ile Asp Ser His Asn Ile Ile Leu Val Gly Glu Val Asp Lys Leu
            820                 825                 830
Lys Ala Lys Val Asn Asn Ser Phe Gln Asn Thr Ile Pro Phe Asn Ile
        835                 840                 845
Phe Ser Tyr Thr Asn Asn Ser Leu Leu Lys Asp Ile Ile Asn Glu Tyr
        850                 855                 860
Phe Asn Asn Ile Asn Asp Ser Lys Ile Leu Ser Leu Gln Asn Arg Lys
865                 870                 875                 880
Asn Thr Leu Val Asp Thr Ser Gly Tyr Asn Ala Glu Val Ser Glu Glu
                885                 890                 895
Gly Asp Val Gln Leu Asn Pro Ile Phe Pro Phe Asp Phe Lys Leu Gly
            900                 905                 910
Ser Ser Gly Glu Asp Arg Gly Lys Val Ile Val Thr Gln Asn Glu Asn
        915                 920                 925
Ile Val Tyr Asn Ser Met Tyr Glu Ser Phe Ser Ile Ser Phe Trp Ile
        930                 935                 940
Arg Ile Asn Lys Trp Val Ser Asn Leu Pro Gly Tyr Thr Ile Ile Asp
945                 950                 955                 960
Ser Val Lys Asn Asn Ser Gly Trp Ser Ile Gly Ile Ile Ser Asn Phe
                965                 970                 975
Leu Val Phe Thr Leu Lys Gln Asn Glu Asp Ser Glu Gln Ser Ile Asn
            980                 985                 990
```

```
Phe Ser Tyr Asp Ile Ser Asn Asn Ala Pro Gly Tyr Asn Lys Trp Phe
            995                 1000                1005

Phe Val Thr Val Thr Asn Asn Met Met Gly Asn Met Lys Ile Tyr
    1010                1015                1020

Ile Asn Gly Lys Leu Ile Asp Thr Ile Lys Val Lys Glu Leu Thr
    1025                1030                1035

Gly Ile Asn Phe Ser Lys Thr Ile Thr Phe Glu Ile Asn Lys Ile
    1040                1045                1050

Pro Asp Thr Gly Leu Ile Thr Ser Asp Ser Asp Asn Ile Asn Met
    1055                1060                1065

Trp Ile Arg Asp Phe Tyr Ile Phe Ala Lys Glu Leu Asp Gly Lys
    1070                1075                1080

Asp Ile Asn Ile Leu Phe Asn Ser Leu Gln Tyr Thr Asn Val Val
    1085                1090                1095

Lys Asp Tyr Trp Gly Asn Asp Leu Arg Tyr Asn Lys Glu Tyr Tyr
    1100                1105                1110

Met Val Asn Ile Asp Tyr Leu Asn Arg Tyr Met Tyr Ala Asn Ser
    1115                1120                1125

Arg Gln Ile Val Phe Asn Thr Arg Arg Asn Asn Asn Asp Phe Asn
    1130                1135                1140

Glu Gly Tyr Lys Ile Ile Ile Lys Arg Ile Arg Gly Asn Thr Asn
    1145                1150                1155

Asp Thr Arg Val Arg Gly Gly Asp Ile Leu Tyr Phe Asp Met Thr
    1160                1165                1170

Ile Asn Asn Lys Ala Tyr Asn Leu Phe Met Lys Asn Glu Thr Met
    1175                1180                1185

Tyr Ala Asp Asn His Ser Thr Glu Asp Ile Tyr Ala Ile Gly Leu
    1190                1195                1200

Arg Glu Gln Thr Lys Asp Ile Asn Asp Asn Ile Ile Phe Gln Ile
    1205                1210                1215

Gln Pro Met Asn Asn Thr Tyr Tyr Tyr Ala Ser Gln Ile Phe Lys
    1220                1225                1230

Ser Asn Phe Asn Gly Glu Asn Ile Ser Gly Ile Cys Ser Ile Gly
    1235                1240                1245

Thr Tyr Arg Phe Arg Leu Gly Gly Asp Trp Tyr Arg His Asn Tyr
    1250                1255                1260

Leu Val Pro Thr Val Lys Gln Gly Asn Tyr Ala Ser Leu Leu Glu
    1265                1270                1275

Ser Thr Ser Thr His Trp Gly Phe Val Pro Val Ser Glu
    1280                1285                1290

<210> SEQ ID NO 4
<211> LENGTH: 1276
<212> TYPE: PRT
<213> ORGANISM: Clostridium botulinum (serotype D)

<400> SEQUENCE: 4

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
                20                  25                  30

Pro Val Lys Ala Phe Met Ile Thr Gln Asn Ile Trp Val Ile Pro Glu
            35                  40                  45

Arg Phe Ser Ser Asp Thr Asn Pro Ser Leu Ser Lys Pro Pro Arg Pro
        50                  55                  60
```

```
Thr Ser Lys Tyr Gln Ser Tyr Tyr Asp Pro Ser Tyr Leu Ser Thr Asp
 65              70                  75                  80

Glu Gln Lys Asp Thr Phe Leu Lys Gly Ile Ile Lys Leu Phe Lys Arg
                 85                  90                  95

Ile Asn Glu Arg Asp Ile Gly Lys Lys Leu Ile Asn Tyr Leu Val Val
             100                 105                 110

Gly Ser Pro Phe Met Gly Asp Ser Ser Thr Pro Glu Asp Thr Phe Asp
             115                 120                 125

Phe Thr Arg His Thr Thr Asn Ile Ala Val Glu Lys Phe Glu Asn Gly
             130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                 165                 170                 175

Gln Gln Ser Asn Pro Ser Phe Glu Gly Phe Gly Thr Leu Ser Ile Leu
             180                 185                 190

Lys Val Ala Pro Glu Phe Leu Leu Thr Phe Ser Asp Val Thr Ser Asn
             195                 200                 205

Gln Ser Ser Ala Val Leu Gly Lys Ser Ile Phe Cys Met Asp Pro Val
210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                 245                 250                 255

Phe Phe Ser Gln Asp Gly Pro Asn Val Gln Phe Glu Glu Leu Tyr Thr
             260                 265                 270

Phe Gly Gly Leu Asp Val Glu Ile Ile Pro Gln Ile Glu Arg Ser Gln
             275                 280                 285

Leu Arg Glu Lys Ala Leu Gly His Tyr Lys Asp Ile Ala Lys Arg Leu
290                 295                 300

Asn Asn Ile Asn Lys Thr Ile Pro Ser Ser Trp Ile Ser Asn Ile Asp
305                 310                 315                 320

Lys Tyr Lys Lys Ile Phe Ser Glu Lys Tyr Asn Phe Asp Lys Asp Asn
                 325                 330                 335

Thr Gly Asn Phe Val Val Asn Ile Asp Lys Phe Asn Ser Leu Tyr Ser
             340                 345                 350

Asp Leu Thr Asn Val Met Ser Glu Val Val Tyr Ser Ser Gln Tyr Asn
             355                 360                 365

Val Lys Asn Arg Thr His Tyr Phe Ser Arg His Tyr Leu Pro Val Phe
370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                 405                 410                 415

Arg Asn Pro Ala Leu Gln Lys Leu Ser Ser Glu Ser Val Val Asp Leu
             420                 425                 430

Phe Thr Lys Val Cys Leu Arg Leu Thr Lys Asn Ser Arg Asp Asp Ser
             435                 440                 445

Thr Cys Ile Lys Val Lys Asn Asn Arg Leu Pro Tyr Val Ala Asp Lys
             450                 455                 460

Asp Ser Ile Ser Gln Glu Ile Phe Glu Asn Lys Ile Ile Thr Asp Glu
465                 470                 475                 480
```

-continued

```
Thr Asn Val Gln Asn Tyr Ser Asp Asn Phe Ser Leu Asp Glu Ser Ile
                485                 490                 495
Leu Asp Gly Gln Val Pro Ile Asn Pro Glu Ile Val Asp Pro Leu Leu
            500                 505                 510
Pro Asn Val Asn Met Glu Pro Leu Asn Leu Pro Gly Glu Glu Ile Val
        515                 520                 525
Phe Tyr Asp Asp Ile Thr Lys Tyr Val Asp Tyr Leu Asn Ser Tyr Tyr
    530                 535                 540
Tyr Leu Glu Ser Gln Lys Leu Ser Asn Asn Val Glu Asn Ile Thr Leu
545                 550                 555                 560
Thr Thr Ser Val Glu Glu Ala Leu Gly Tyr Ser Asn Lys Ile Tyr Thr
                565                 570                 575
Phe Leu Pro Ser Leu Ala Glu Lys Val Asn Lys Gly Val Gln Ala Gly
            580                 585                 590
Leu Phe Leu Asn Trp Ala Asn Glu Val Val Glu Asp Phe Thr Thr Asn
        595                 600                 605
Ile Met Lys Lys Asp Thr Leu Asp Lys Ile Ser Asp Val Ser Val Ile
    610                 615                 620
Ile Pro Tyr Ile Gly Pro Ala Leu Asn Ile Gly Asn Ser Ala Leu Arg
625                 630                 635                 640
Gly Asn Phe Lys Gln Ala Phe Ala Thr Ala Gly Val Ala Phe Leu Leu
                645                 650                 655
Glu Gly Phe Pro Glu Phe Thr Ile Pro Ala Leu Gly Val Phe Thr Phe
            660                 665                 670
Tyr Ser Ser Ile Gln Glu Arg Glu Lys Ile Ile Lys Thr Ile Glu Asn
        675                 680                 685
Cys Leu Glu Gln Arg Val Lys Arg Trp Lys Asp Ser Tyr Gln Trp Met
    690                 695                 700
Val Ser Asn Trp Leu Ser Arg Ile Thr Thr Gln Phe Asn His Ile Asn
705                 710                 715                 720
Tyr Gln Met Tyr Asp Ser Leu Ser Tyr Gln Ala Asp Ala Ile Lys Ala
                725                 730                 735
Lys Ile Asp Leu Glu Tyr Lys Lys Tyr Ser Gly Ser Asp Lys Glu Asn
            740                 745                 750
Ile Lys Ser Gln Val Glu Asn Leu Lys Asn Ser Leu Asp Val Lys Ile
        755                 760                 765
Ser Glu Ala Met Asn Asn Ile Asn Lys Phe Ile Arg Glu Cys Ser Val
    770                 775                 780
Thr Tyr Leu Phe Lys Asn Met Leu Pro Lys Val Ile Asp Glu Leu Asn
785                 790                 795                 800
Lys Phe Asp Leu Arg Thr Lys Thr Glu Leu Ile Asn Leu Ile Asp Ser
                805                 810                 815
His Asn Ile Ile Leu Val Gly Glu Val Asp Arg Leu Lys Ala Lys Val
            820                 825                 830
Asn Glu Ser Phe Glu Asn Thr Met Pro Phe Asn Ile Phe Ser Tyr Thr
        835                 840                 845
Asn Asn Ser Leu Leu Lys Asp Ile Ile Asn Glu Tyr Phe Asn Ser Ile
    850                 855                 860
Asn Asp Ser Lys Ile Leu Ser Leu Gln Asn Lys Lys Asn Ala Leu Val
865                 870                 875                 880
Asp Thr Ser Gly Tyr Asn Ala Glu Val Arg Val Gly Asp Asn Val Gln
                885                 890                 895
```

-continued

Leu Asn Thr Ile Tyr Thr Asn Asp Phe Lys Leu Ser Ser Gly Asp
            900                 905                 910

Lys Ile Ile Val Asn Leu Asn Asn Ile Leu Tyr Ser Ala Ile Tyr
            915                 920                 925

Glu Asn Ser Ser Val Ser Phe Trp Ile Lys Ile Ser Lys Asp Leu Thr
            930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
            965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
            995                 1000                1005

Asn Asn Ile Met Gly Tyr Met Lys Leu Tyr Ile Asn Gly Glu Leu
            1010                1015                1020

Lys Gln Ser Gln Lys Ile Glu Asp Leu Asp Glu Val Lys Leu Asp
            1025                1030                1035

Lys Thr Ile Val Phe Gly Ile Asp Glu Asn Ile Asp Glu Asn Gln
            1040                1045                1050

Met Leu Trp Ile Arg Asp Phe Asn Ile Phe Ser Lys Glu Leu Ser
            1055                1060                1065

Asn Glu Asp Ile Asn Ile Val Tyr Glu Gly Gln Ile Leu Arg Asn
            1070                1075                1080

Val Ile Lys Asp Tyr Trp Gly Asn Pro Leu Lys Phe Asp Thr Glu
            1085                1090                1095

Tyr Tyr Ile Ile Asn Asp Asn Tyr Ile Asp Arg Tyr Ile Ala Pro
            1100                1105                1110

Glu Ser Asn Val Leu Val Leu Val Arg Tyr Pro Asp Arg Ser Lys
            1115                1120                1125

Leu Tyr Thr Gly Asn Pro Ile Thr Ile Lys Ser Val Ser Asp Lys
            1130                1135                1140

Asn Pro Tyr Ser Arg Ile Leu Asn Gly Asp Asn Ile Ile Leu His
            1145                1150                1155

Met Leu Tyr Asn Ser Arg Lys Tyr Met Ile Ile Arg Asp Thr Asp
            1160                1165                1170

Thr Ile Tyr Ala Thr Gln Gly Gly Glu Cys Ser Gln Asn Cys Val
            1175                1180                1185

Tyr Ala Leu Lys Leu Gln Ser Asn Leu Gly Asn Tyr Gly Ile Gly
            1190                1195                1200

Ile Phe Ser Ile Lys Asn Ile Val Ser Lys Asn Lys Tyr Cys Ser
            1205                1210                1215

Gln Ile Phe Ser Ser Phe Arg Glu Asn Thr Met Leu Leu Ala Asp
            1220                1225                1230

Ile Tyr Lys Pro Trp Arg Phe Ser Phe Lys Asn Ala Tyr Thr Pro
            1235                1240                1245

Val Ala Val Thr Asn Tyr Glu Thr Lys Leu Leu Ser Thr Ser Ser
            1250                1255                1260

Phe Trp Lys Phe Ile Ser Arg Asp Pro Gly Trp Val Glu
            1265                1270                1275

<210> SEQ ID NO 5
<211> LENGTH: 1251
<212> TYPE: PRT
<213> ORGANISM: Clostridium botulinum (serotype E)

<400> SEQUENCE: 5

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380
```

-continued

```
Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
            405                 410                 415

Ser Val Lys Gly Ile Arg Lys Ser Ile Cys Ile Glu Ile Asn Asn Gly
        420                 425                 430

Glu Leu Phe Phe Val Ala Ser Glu Asn Ser Tyr Asn Asp Asp Asn Ile
    435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
        500                 505                 510

Asp Val Asn Glu Leu Asn Val Phe Phe Tyr Leu Asp Ala Gln Lys Val
    515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
        580                 585                 590

Val Asp Lys Ile Ala Asp Ile Ser Ile Val Val Pro Tyr Ile Gly Leu
    595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
        660                 665                 670

Glu Arg Asp Glu Lys Trp Lys Glu Val Tyr Ser Phe Ile Val Ser Asn
    675                 680                 685

Trp Met Thr Lys Ile Asn Thr Gln Phe Asn Lys Arg Lys Glu Gln Met
690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Lys Gln Ile Glu Asn Glu Leu Asn Gln Lys Val Ser
        740                 745                 750

Ile Ala Met Asn Asn Ile Asp Arg Phe Leu Thr Glu Ser Ser Ile Ser
    755                 760                 765

Tyr Leu Met Lys Leu Ile Asn Glu Val Lys Ile Asn Lys Leu Arg Glu
770                 775                 780

Tyr Asp Glu Asn Val Lys Thr Tyr Leu Leu Asn Tyr Ile Ile Gln His
785                 790                 795                 800
```

-continued

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Leu Gln Asp Asn Ala Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
            995                 1000                1005

Gly Asn Leu Ile Asp Gln Lys Ser Ile Leu Asn Leu Gly Asn Ile
    1010                1015                1020

His Val Ser Asp Asn Ile Leu Phe Lys Ile Val Asn Cys Ser Tyr
    1025                1030                1035

Thr Arg Tyr Ile Gly Ile Arg Tyr Phe Asn Ile Phe Asp Lys Glu
    1040                1045                1050

Leu Asp Glu Thr Glu Ile Gln Thr Leu Tyr Ser Asn Glu Pro Asn
    1055                1060                1065

Thr Asn Ile Leu Lys Asp Phe Trp Gly Asn Tyr Leu Leu Tyr Asp
    1070                1075                1080

Lys Glu Tyr Tyr Leu Leu Asn Val Leu Lys Pro Asn Asn Phe Ile
    1085                1090                1095

Asp Arg Arg Lys Asp Ser Thr Leu Ser Ile Asn Asn Ile Arg Ser
    1100                1105                1110

Thr Ile Leu Leu Ala Asn Arg Leu Tyr Ser Gly Ile Lys Val Lys
    1115                1120                1125

Ile Gln Arg Val Asn Asn Ser Ser Thr Asn Asp Asn Leu Val Arg
    1130                1135                1140

Lys Asn Asp Gln Val Tyr Ile Asn Phe Val Ala Ser Lys Thr His
    1145                1150                1155

Leu Phe Pro Leu Tyr Ala Asp Thr Ala Thr Thr Asn Lys Glu Lys
    1160                1165                1170

Thr Ile Lys Ile Ser Ser Ser Gly Asn Arg Phe Asn Gln Val Val
    1175                1180                1185

Val Met Asn Ser Val Gly Asn Asn Thr Met Asn Phe Lys Asn Asn
    1190                1195                1200

```
Asn Gly Asn Asn Ile Gly Leu Leu Gly Phe Lys Ala Asp Thr Val
    1205                1210                1215

Val Ala Ser Thr Trp Tyr Tyr Thr His Met Arg Asp His Thr Asn
    1220                1225                1230

Ser Asn Gly Cys Phe Trp Asn Phe Ile Ser Glu Glu His Gly Trp
    1235                1240                1245

Gln Glu Lys
    1250

<210> SEQ ID NO 6
<211> LENGTH: 1277
<212> TYPE: PRT
<213> ORGANISM: Clostridium botulinum (serotype F)

<400> SEQUENCE: 6

Met Pro Val Val Ile Asn Ser Phe Asn Tyr Asn Asp Pro Val Asn Asp
1               5                   10                  15

Asp Thr Ile Leu Tyr Met Gln Ile Pro Tyr Glu Glu Lys Ser Lys Lys
                20                  25                  30

Tyr Tyr Lys Ala Phe Glu Ile Met Arg Asn Val Trp Ile Ile Pro Glu
                35                  40                  45

Arg Asn Thr Ile Gly Thr Asp Pro Ser Asp Phe Asp Pro Pro Ala Ser
            50                  55                  60

Leu Glu Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Glu Val Leu Leu Gln Glu Ile Ser
            100                 105                 110

Tyr Ala Lys Pro Tyr Leu Gly Asn Glu His Thr Pro Ile Asn Glu Phe
        115                 120                 125

His Pro Val Thr Arg Thr Thr Ser Val Asn Ile Lys Ser Ser Thr Asn
    130                 135                 140

Val Lys Ser Ser Ile Ile Leu Asn Leu Leu Val Leu Gly Ala Gly Pro
145                 150                 155                 160

Asp Ile Phe Glu Asn Ser Ser Tyr Pro Val Arg Lys Leu Met Asp Ser
                165                 170                 175

Gly Gly Val Tyr Asp Pro Ser Asn Asp Gly Phe Gly Ser Ile Asn Ile
            180                 185                 190

Val Thr Phe Ser Pro Glu Tyr Glu Tyr Thr Phe Asn Asp Ile Ser Gly
        195                 200                 205

Gly Tyr Asn Ser Ser Thr Glu Ser Phe Ile Ala Asp Pro Ala Ile Ser
    210                 215                 220

Leu Ala His Glu Leu Ile His Ala Leu His Gly Leu Tyr Gly Ala Arg
225                 230                 235                 240

Gly Val Thr Tyr Lys Glu Thr Ile Lys Val Lys Gln Ala Pro Leu Met
                245                 250                 255

Ile Ala Ile Lys Pro Ile Arg Leu Glu Glu Phe Leu Thr Phe Gly Gly
            260                 265                 270

Gln Asp Leu Asn Ile Ile Thr Ser Ala Met Lys Glu Lys Ile Tyr Asn
        275                 280                 285

Asn Leu Leu Ala Asn Tyr Glu Lys Ile Ala Thr Arg Leu Ser Arg Val
    290                 295                 300

Asn Ser Ala Pro Pro Glu Tyr Asp Ile Asn Glu Tyr Lys Asp Tyr Phe
305                 310                 315                 320
```

-continued

```
Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Leu Lys Val Pro Asn Leu Leu Asp Asp Asp
370                 375                 380

Ile Tyr Thr Val Ser Glu Gly Phe Asn Ile Gly Asn Leu Ala Val Asn
385                 390                 395                 400

Asn Arg Gly Gln Asn Ile Lys Leu Asn Pro Lys Ile Ile Asp Ser Ile
            405                 410                 415

Pro Asp Lys Gly Leu Val Glu Lys Ile Val Lys Phe Cys Lys Ser Val
        420                 425                 430

Ile Pro Arg Lys Gly Thr Lys Ala Pro Pro Arg Leu Cys Ile Arg Val
    435                 440                 445

Asn Asn Arg Glu Leu Phe Phe Val Ala Ser Glu Ser Ser Tyr Asn Glu
450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
            485                 490                 495

Glu Thr Ile Pro Gln Ile Ser Asn Gln Thr Leu Asn Thr Leu Val Gln
        500                 505                 510

Asp Asp Ser Tyr Val Pro Arg Tyr Asp Ser Asn Gly Thr Ser Glu Ile
    515                 520                 525

Glu Glu His Asn Val Val Asp Leu Asn Val Phe Phe Tyr Leu His Ala
530                 535                 540

Gln Lys Val Pro Glu Gly Glu Thr Asn Ile Ser Leu Thr Ser Ser Ile
545                 550                 555                 560

Asp Thr Ala Leu Ser Glu Glu Ser Gln Val Tyr Thr Phe Phe Ser Ser
            565                 570                 575

Glu Phe Ile Asn Thr Ile Asn Lys Pro Val His Ala Ala Leu Phe Ile
        580                 585                 590

Ser Trp Ile Asn Gln Val Ile Arg Asp Phe Thr Thr Glu Ala Thr Gln
    595                 600                 605

Lys Ser Thr Phe Asp Lys Ile Ala Asp Ile Ser Leu Val Val Pro Tyr
610                 615                 620

Val Gly Leu Ala Leu Asn Ile Gly Asn Glu Val Gln Lys Glu Asn Phe
625                 630                 635                 640

Lys Glu Ala Phe Glu Leu Leu Gly Ala Gly Ile Leu Leu Glu Phe Val
            645                 650                 655

Pro Glu Leu Leu Ile Pro Thr Ile Leu Val Phe Thr Ile Lys Ser Phe
        660                 665                 670

Ile Gly Ser Ser Glu Asn Lys Asn Lys Ile Ile Lys Ala Ile Asn Asn
    675                 680                 685

Ser Leu Met Glu Arg Glu Thr Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735
```

```
Val Ile Glu Tyr Lys Tyr Asn Asn Tyr Thr Ser Asp Glu Arg Asn Arg
            740                 745                 750

Leu Glu Ser Glu Tyr Asn Ile Asn Asn Ile Arg Glu Glu Leu Asn Lys
            755                 760                 765

Lys Val Ser Leu Ala Met Glu Asn Ile Glu Arg Phe Ile Thr Glu Ser
            770                 775                 780

Ser Ile Phe Tyr Leu Met Lys Leu Ile Asn Glu Ala Lys Val Ser Lys
785                 790                 795                 800

Leu Arg Glu Tyr Asp Glu Gly Val Lys Glu Tyr Leu Leu Asp Tyr Ile
            805                 810                 815

Ser Glu His Arg Ser Ile Leu Gly Asn Ser Val Gln Glu Leu Asn Asp
            820                 825                 830

Leu Val Thr Ser Thr Leu Asn Asn Ser Ile Pro Phe Glu Leu Ser Ser
            835                 840                 845

Tyr Thr Asn Asp Lys Ile Leu Ile Leu Tyr Phe Asn Lys Leu Tyr Lys
            850                 855                 860

Lys Ile Lys Asp Asn Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asp
            885                 890                 895

Val Tyr Ile Tyr Ser Thr Asn Arg Asn Gln Phe Gly Ile Tyr Ser Ser
            900                 905                 910

Lys Pro Ser Glu Val Asn Ile Ala Gln Asn Asn Asp Ile Ile Tyr Asn
            915                 920                 925

Gly Arg Tyr Gln Asn Phe Ser Ile Ser Phe Trp Val Arg Ile Pro Lys
            930                 935                 940

Tyr Phe Asn Lys Val Asn Leu Asn Asn Glu Tyr Thr Ile Ile Asp Cys
945                 950                 955                 960

Ile Arg Asn Asn Asn Ser Gly Trp Lys Ile Ser Leu Asn Tyr Asn Lys
            965                 970                 975

Ile Ile Trp Thr Leu Gln Asp Thr Ala Gly Asn Asn Gln Lys Leu Val
            980                 985                 990

Phe Asn Tyr Thr Gln Met Ile Ser  Ile Ser Asp Tyr Ile  Asn Lys Trp
            995                 1000                1005

Ile Phe  Val Thr Ile Thr Asn  Asn Arg Leu Gly Asn  Ser Arg Ile
1010                1015                1020

Tyr Ile  Asn Gly Asn Leu Ile  Asp Glu Lys Ser Ile  Ser Asn Leu
1025                1030                1035

Gly Asp  Ile His Val Ser Asp  Asn Ile Leu Phe Lys  Ile Val Gly
1040                1045                1050

Cys Asn  Asp Thr Arg Tyr Val  Gly Ile Arg Tyr Phe  Lys Val Phe
1055                1060                1065

Asp Thr  Glu Leu Gly Lys Thr  Glu Ile Glu Thr Leu  Tyr Ser Asp
1070                1075                1080

Glu Pro  Asp Pro Ser Ile Leu  Lys Asp Phe Trp Gly  Asn Tyr Leu
1085                1090                1095

Leu Tyr  Asn Lys Arg Tyr Tyr  Leu Leu Asn Leu Leu  Arg Thr Asp
1100                1105                1110

Lys Ser  Ile Thr Gln Asn Ser  Asn Phe Leu Asn Ile  Asn Gln Gln
1115                1120                1125

Arg Gly  Val Tyr Gln Lys Pro  Asn Ile Phe Ser Asn  Thr Arg Leu
1130                1135                1140
```

```
Tyr Thr Gly Val Glu Val Ile Ile Arg Lys Asn Gly Ser Thr Asp
    1145                1150                1155

Ile Ser Asn Thr Asp Asn Phe Val Arg Lys Asn Asp Leu Ala Tyr
    1160                1165                1170

Ile Asn Val Val Asp Arg Asp Val Glu Tyr Arg Leu Tyr Ala Asp
    1175                1180                1185

Ile Ser Ile Ala Lys Pro Glu Lys Ile Ile Lys Leu Ile Arg Thr
    1190                1195                1200

Ser Asn Ser Asn Asn Ser Leu Gly Gln Ile Ile Val Met Asp Ser
    1205                1210                1215

Ile Gly Asn Asn Thr Met Asn Phe Gln Asn Asn Gly Gly Asn
    1220                1225                1230

Ile Gly Leu Leu Gly Phe His Ser Asn Asn Leu Val Ala Ser Ser
    1235                1240                1245

Trp Tyr Tyr Asn Asn Ile Arg Lys Asn Thr Ser Ser Asn Gly Cys
    1250                1255                1260

Phe Trp Ser Phe Ile Ser Lys Glu His Gly Trp Gln Glu Asn
    1265                1270                1275
```

```
<210> SEQ ID NO 7
<211> LENGTH: 1297
<212> TYPE: PRT
<213> ORGANISM: Clostridium botulinum (serotype G)

<400> SEQUENCE: 7

Met Pro Val Asn Ile Lys Asn Phe Asn Tyr Asn Asp Pro Ile Asn Asn
1               5                   10                  15

Asp Asp Ile Ile Met Met Glu Pro Phe Asn Asp Pro Gly Pro Gly Thr
                20                  25                  30

Tyr Tyr Lys Ala Phe Arg Ile Ile Asp Arg Ile Trp Ile Val Pro Glu
            35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
    115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
    195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240
```

```
Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
            260                 265                 270

Gly Gly His Asp Pro Ser Val Ile Ser Pro Ser Thr Asp Met Asn Ile
        275                 280                 285

Tyr Asn Lys Ala Leu Gln Asn Phe Gln Asp Ile Ala Asn Arg Leu Asn
    290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
            340                 345                 350

Phe Gly Phe Thr Glu Thr Asn Leu Ala Gly Glu Tyr Gly Ile Lys Thr
        355                 360                 365

Arg Tyr Ser Tyr Phe Ser Glu Tyr Leu Pro Pro Ile Lys Thr Glu Lys
    370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
            420                 425                 430

Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
    450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
            500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
    530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Asn Lys Val Tyr Thr
                565                 570                 575

Phe Phe Ser Thr Asn Leu Val Glu Lys Ala Asn Thr Val Val Gly Ala
            580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
    610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655
```

-continued

Met Glu Phe Ile Pro Glu Leu Ile Val Pro Ile Val Gly Phe Phe Thr
              660                 665                 670

Leu Glu Ser Tyr Val Gly Asn Lys Gly His Ile Ile Met Thr Ile Ser
          675                 680                 685

Asn Ala Leu Lys Lys Arg Asp Gln Lys Trp Thr Asp Met Tyr Gly Leu
      690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
              725                 730                 735

Lys Ile Ile Glu Asp Gln Tyr Asn Arg Tyr Ser Glu Glu Asp Lys Met
              740                 745                 750

Asn Ile Asn Ile Asp Phe Asn Asp Ile Asp Phe Lys Leu Asn Gln Ser
          755                 760                 765

Ile Asn Leu Ala Ile Asn Asn Ile Asp Asp Phe Ile Asn Gln Cys Ser
      770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
              805                 810                 815

Thr Asn Glu Leu Tyr Leu Leu Asp Glu Val Asn Ile Leu Lys Ser Lys
              820                 825                 830

Val Asn Arg His Leu Lys Asp Ser Ile Pro Phe Asp Leu Ser Leu Tyr
          835                 840                 845

Thr Lys Asp Thr Ile Leu Ile Gln Val Phe Asn Asn Tyr Ile Ser Asn
      850                 855                 860

Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
              885                 890                 895

Ile Phe Asn Asp Ile Gly Asn Gly Gln Phe Lys Leu Asn Asn Ser Glu
          900                 905                 910

Asn Ser Asn Ile Thr Ala His Gln Ser Lys Phe Val Val Tyr Asp Ser
      915                 920                 925

Met Phe Asp Asn Phe Ser Ile Asn Phe Trp Val Arg Thr Pro Lys Tyr
930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
              965                 970                 975

Arg Ile Ile Trp Thr Leu Ile Asp Val Asn Ala Lys Ser Lys Ser Ile
              980                 985                 990

Phe Phe Glu Tyr Ser Ile Lys Asp Asn Ile Ser Asp Tyr Ile Asn Lys
          995                 1000                1005

Trp Phe Ser Ile Thr Ile Thr Asn Asp Arg Leu Gly Asn Ala Asn
      1010                1015                1020

Ile Tyr Ile Asn Gly Ser Leu Lys Lys Ser Glu Lys Ile Leu Asn
      1025                1030                1035

Leu Asp Arg Ile Asn Ser Ser Asn Asp Ile Asp Phe Lys Leu Ile
      1040                1045                1050

Asn Cys Thr Asp Thr Thr Lys Phe Val Trp Ile Lys Asp Phe Asn
      1055                1060                1065

```
Ile Phe Gly Arg Glu Leu Asn Ala Thr Glu Val Ser  Ser Leu Tyr
    1070                1075                1080

Trp Ile Gln Ser Ser Thr Asn Thr Leu Lys Asp Phe  Trp Gly Asn
    1085                1090                1095

Pro Leu Arg Tyr Asp Thr Gln Tyr Tyr Leu Phe Asn  Gln Gly Met
    1100                1105                1110

Gln Asn Ile Tyr Ile Lys Tyr Phe Ser Lys Ala Ser  Met Gly Glu
    1115                1120                1125

Thr Ala Pro Arg Thr Asn Phe Asn Asn Ala Ala Ile  Asn Tyr Gln
    1130                1135                1140

Asn Leu Tyr Leu Leu Arg Phe Ile Ile Lys Lys Ala  Ser Asn Ser
    1145                1150                1155

Arg Asn Ile Asn Asn Asp Asn Ile Val Arg Glu Gly  Asp Tyr Ile
    1160                1165                1170

Tyr Leu Asn Ile Asp Asn Ile Ser Asp Glu Ser Tyr  Arg Val Tyr
    1175                1180                1185

Val Leu Val Asn Ser Lys Glu Ile Gln Thr Gln Leu  Phe Leu Ala
    1190                1195                1200

Pro Ile Asn Asp Asp Pro Thr Phe Tyr Asp Val Leu  Gln Ile Gly
    1205                1210                1215

Lys Lys Tyr Tyr Glu Lys Thr Thr Tyr Asn Cys Gln  Ile Leu Cys
    1220                1225                1230

Glu Lys Asp Thr Lys Thr Phe Gly Leu Phe Gly Ile  Gly Lys Phe
    1235                1240                1245

Val Lys Asp Tyr Gly Tyr Val Trp Asp Thr Tyr Asp  Asn Tyr Phe
    1250                1255                1260

Cys Ile Ser Gln Trp Tyr Leu Arg Arg Ile Ser Glu  Asn Ile Asn
    1265                1270                1275

Lys Leu Arg Leu Gly Cys Asn Trp Gln Phe Ile Pro  Val Asp Glu
    1280                1285                1290

Gly Trp Thr Glu
    1295

<210> SEQ ID NO 8
<211> LENGTH: 8
<212> TYPE: PRT
<213> ORGANISM: Artificial Sequence
<220> FEATURE:
<223> OTHER INFORMATION: metalloprotease motif
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (6)..(7)
<223> OTHER INFORMATION: Xaa can be any naturally occurring amino acid

<400> SEQUENCE: 8

His Glu Xaa Xaa His Xaa Xaa His
1               5

<210> SEQ ID NO 9
<211> LENGTH: 5
<212> TYPE: PRT
<213> ORGANISM: Artificial Sequence
<220> FEATURE:
<223> OTHER INFORMATION: enterokinase cleavage site
```

```
<400> SEQUENCE: 9

Asp Asp Asp Asp Lys
1               5

<210> SEQ ID NO 10
<211> LENGTH: 34
<212> TYPE: PRT
<213> ORGANISM: Artificial Sequence
<220> FEATURE:
<223> OTHER INFORMATION: hexahistidine affinity tag

<400> SEQUENCE: 10

Met Pro Met Leu Ser Ala Ile Val Leu Tyr Val Leu Leu Ala Ala Ala
1               5                   10                  15

Ala His Ser Ala Phe Ala Ala Met Val His His His His His His Ser
            20                  25                  30

Ala Ser
```